US010827694B2

(12) United States Patent
Aidun

(10) Patent No.: US 10,827,694 B2
(45) Date of Patent: Nov. 10, 2020

(54) PLANT PROPAGULE ROOT-GROWING DEVICE

(71) Applicant: Georgia Tech Research Corporation, Atlanta, GA (US)

(72) Inventor: Cyrus Aidun, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 659 days.

(21) Appl. No.: 15/537,033

(22) PCT Filed: Dec. 21, 2015

(86) PCT No.: PCT/IB2015/059811
§ 371 (c)(1),
(2) Date: Jun. 16, 2017

(87) PCT Pub. No.: WO2016/098083
PCT Pub. Date: Jun. 23, 2016

(65) Prior Publication Data
US 2017/0339856 A1    Nov. 30, 2017

Related U.S. Application Data

(60) Provisional application No. 62/094,326, filed on Dec. 19, 2014.

(30) Foreign Application Priority Data

Apr. 15, 2015    (SE) ........................................ 1550454

(51) Int. Cl.
*A01H 4/00*          (2006.01)
*C12N 5/00*          (2006.01)
(Continued)

(52) U.S. Cl.
CPC ............... *A01H 4/005* (2013.01); *A01H 4/00* (2013.01); *A01H 4/001* (2013.01); *C12N 5/0025* (2013.01); *C12M 1/00* (2013.01); *C12N 5/04* (2013.01)

(58) Field of Classification Search
CPC ...... C12N 5/0025; C12N 5/0018; C12N 5/00; C12N 5/04; C12M 1/00; A01H 4/005; A01H 4/00; A01H 4/001
See application file for complete search history.

(56) References Cited

U.S. PATENT DOCUMENTS

| 4,763,442 A | 8/1988 | Saeger |
| 5,142,814 A | 9/1992 | Guidry |

(Continued)

FOREIGN PATENT DOCUMENTS

| GB | 1041133 | 9/1966 |
| GB | 2416472 | 2/2006 |

(Continued)

OTHER PUBLICATIONS

International Search Report in International Application No. PCT/IB2015/059811, dated Mar. 31, 2016, 13 pages.

(Continued)

*Primary Examiner* — Christopher J. Novosad
(74) *Attorney, Agent, or Firm* — Troutman Pepper Hamilton Sanders LLP; Ryan A. Schneider

(57) ABSTRACT

Devices for directionally placing a plant propagule (2) inside a tubular hollow member (3), including a platform element (20) arranged such that a foldable member (1) can be placed thereon; an actuating dispensing arrangement {90a, 90b,
(Continued)

100) for placing a foldable member (1) on the platform element (20); an arrangement (40)/(40a) for placing a plant propagule (2) on a foldable member (1) placed on the platform element (20); optionally, including a way (150) for identifying an imaginary line (9) on the foldable member (1) stretching through the root forming end (7) to the shoot forming end (8) of the propagule (2) being directionally placed during operation; an actuating folding arrangement {30, 80}/(120/80) for folding the foldable member (1) along said imaginary line (9) to form a folded foldable member (la); an actuating dispensing arrangement (180) for providing a tubular hollow member (3) having a first open end (4); and an actuating placing arrangement {30, 80}/(120/80) for placing said folded foldable member (la) into the tubular hollow member (3) through the first open end (4). Related methods for handling plant propagules, in particular somatic plant embryos.

30 Claims, 9 Drawing Sheets

(51) Int. Cl.
*C12M 1/00* (2006.01)
*C12N 5/04* (2006.01)

(56) References Cited

U.S. PATENT DOCUMENTS

| | | |
|---|---|---|
| 5,573,558 A | 11/1996 | Huang |
| 5,787,824 A | 8/1998 | Kohno |
| 8,001,723 B2 | 8/2011 | Tamura et al. |
| 2011/0153093 A1 | 6/2011 | Aidun |
| 2012/0202289 A1 | 8/2012 | Aidun |
| 2013/0192133 A1 | 8/2013 | Chodula |

FOREIGN PATENT DOCUMENTS

| | | |
|---|---|---|
| JP | 2001320914 | 11/2001 |
| JP | 3459616 | 12/2001 |
| JP | 2002-017167 | 1/2002 |
| JP | 2003-047332 A | 2/2003 |
| WO | WO 2000/00007 | 1/2000 |
| WO | WO 2003/022034 | 3/2003 |
| WO | WO 2009/126758 | 10/2009 |
| WO | WO 2011/042888 | 4/2011 |
| WO | WO 2015/097603 | 7/2015 |

OTHER PUBLICATIONS

International-Type Search Report in National Application No. 1550454-1, dated Dec. 3, 2015, 5 pages.
MarineLab's Research Projects & Partnerships, Available on the Internet URL<https://marinelabresearch.wordpress.com/page/6/>, Oct. 25, 2012, 15 pages.

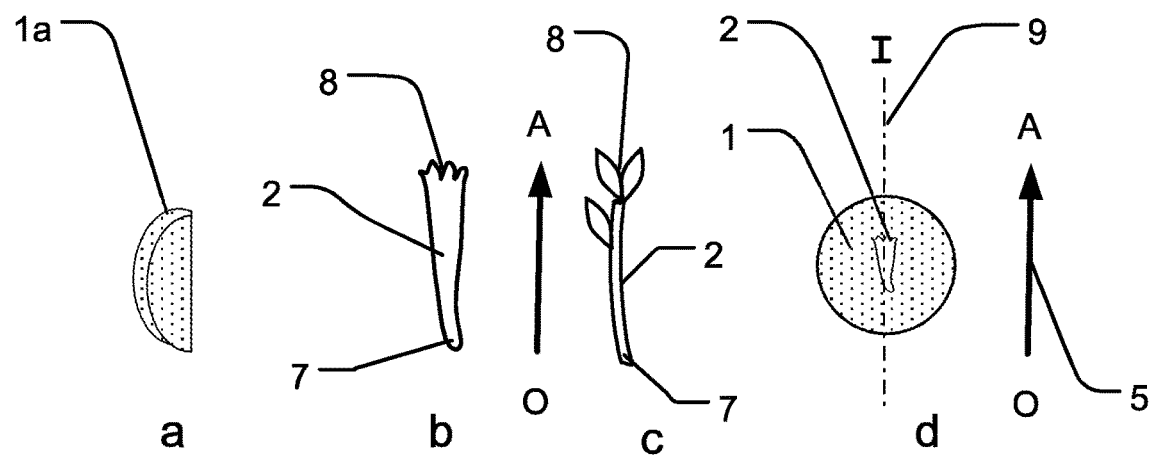
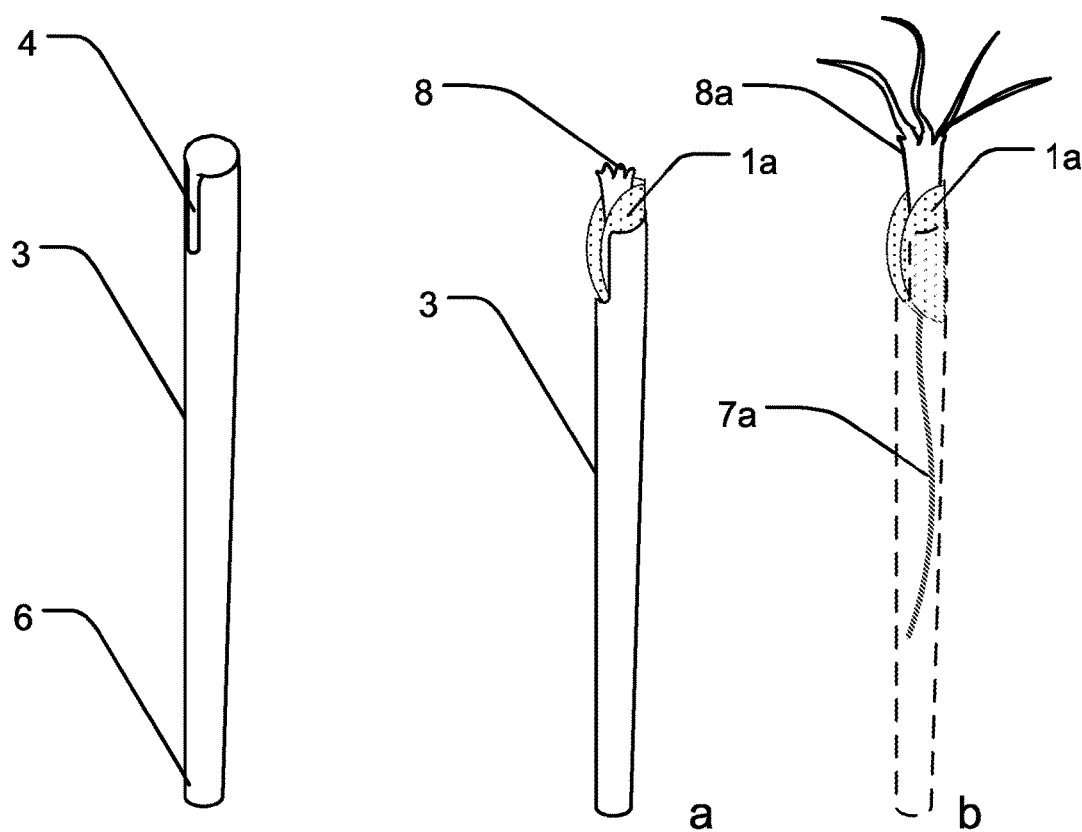
Fig 1
Fig 2
Fig 3

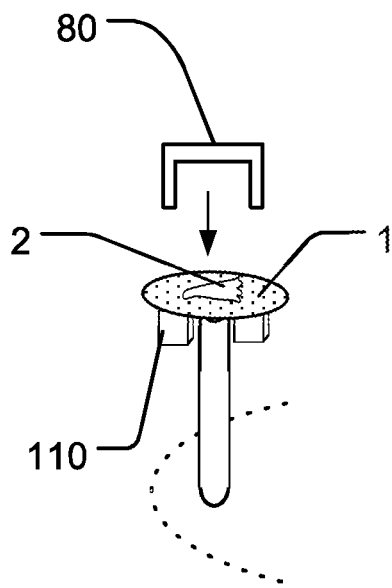
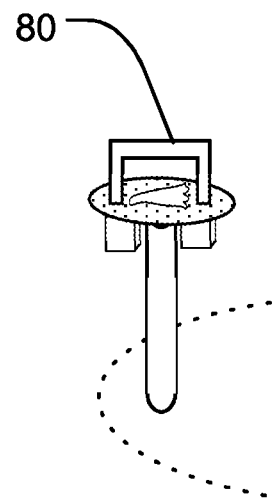
Fig 7 A
Fig 7 B
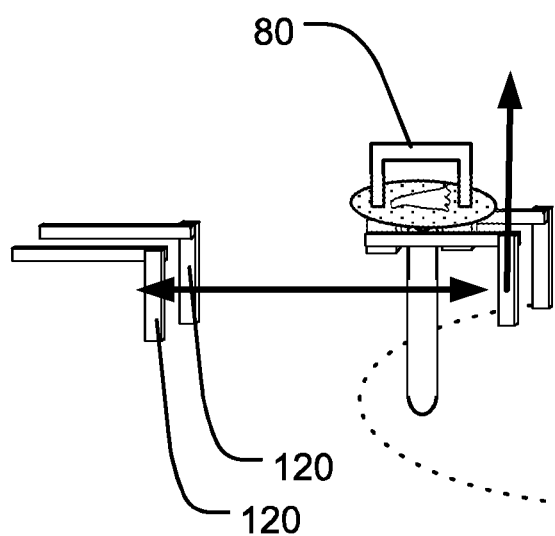
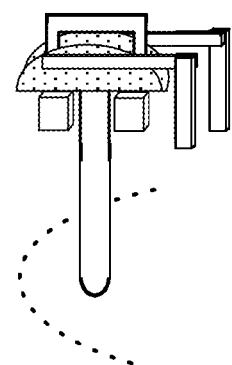
Fig 7 C
Fig 7 D

PLANT PROPAGULE ROOT-GROWING DEVICE

CROSS-REFERENCE TO RELATED APPLICATIONS

This application is a National Stage application under 35 U.S.C. § 371 of International Application No. PCT/IB2015/059811, having an International Filing Date of Dec. 21, 2015, which claims the benefit of Sweden Application No. 1550454-1 filed on Apr. 15, 2015 and U.S. Provisional Ser. No. 62/094,326 filed Dec. 19, 2014. The disclosures of each of these applications are incorporated herein by reference in their entireties.

TECHNICAL FIELD

The invention relates to the field of plant propagule formation and planting, in particular to devices and methods for somatic embryo handling, storage, germination and planting.

BACKGROUND

The use of cuttings is a well-established method for propagation of plants, and it is well known that some plants are easier to propagate than others. In forestry replantation for example, there is need for large numbers of trees with good growth properties. Eucalyptus (*Eucalyptus* sp.) and Poplar (*Populus* sp.) are two examples of trees which today are propagated by cuttings. Other trees, like conifers such as pine, spruce and lark of different species are more difficult or impossible to propagate by cutting. An alternative method for large scale propagation of plants difficult to propagate with cuttings is to use somatic embryogenesis.

Cuttings generally lack a root when they are planted. Somatic embryos develop a root at a late stage and when transferred to a proper light and medium the shoot will develop.

Several methods and devices have been developed for planting small plants. In U.S. Pat. No. 5,142,814 a planting device is disclosed where small plants with well-developed roots within a plug of soil are transported in water and then planted in soil in a tray. The device as disclosed can handle multiple plants. In U.S. Pat. No. 5,573,558 a similar device and method are disclosed for planting plants with well-developed roots.

A problem with planting small plants, germinating somatic embryos or cuttings with a limited developed root is the fragility of the root. These is a high risk that the root of the plant propagule is damaged when planted in the substrate, whereby the fraction of viable plantlets may be low.

PCT/IB2014/067084 discloses a method and a device for planting plant propagules placed in a hollow member. The hollow member is drawn through a growth substrate such as soil, whereby the plant propagules are dislodged from the hollow members and planted in the hole left by the hollow member.

U.S. Pat. No. 5,787,824A discloses a method for planting plantlets at a defined direction. The method comprises planting gel-coated seeds, inducing the seeds sprout a root and then sowing the seeds with the tip of the root facing downward, using a hollow auxiliary tool such as a hollow cylinder.

JP 2003047332A discloses a manual method for growing a root from cuttings, involving wrapping in a biodegradable sheet followed by soil cultivation and/or aquaculture.

US 2013/192133 A1 discloses an automated method for placing cuttings inside an envelope made of biodegradable material such as paper.

Handling of plant propagules in a fluid steam is disclosed e.g. in WO 2011/042888 and US 2011/153093.

There is a continued need for planting methods and devices that can be used to automatize the planting process, in order to increase the throughput of planted propagules.

It is an object of the present invention to provide an improved or at least alternative solution for handling plant propagules.

Definitions

The term "plant propagule" refers to a plant, a part of a plant or a vegetative part of a plant with a root forming end and a shoot forming end. A plant propagule can be grown outdoors, indoors or cultured in vitro. Plant propagule includes plants germinated from seeds, somatic embryos and in vitro grown shoots from calluses or cuttings, but not the seed itself.

The term "root forming end" refers to the end of a plant propagule that will form a root when placed in a suitable substrate under appropriate conditions.

The term "shoot forming end" refers to the end of a plant propagule with a shoot apical meristem (SAM), which has the capacity develop into buds, leaves or cotyledons. The cotyledon is the shoot forming end of somatic embryos.

The term "cuttings" refers to any part of a plant that will form roots when placed in appropriate substrate under suitable conditions.

The term "growth substrate" refers to a material in which a plant propagule can root and grow, such as peat moss, soil, solid or semisolid medium.

SUMMARY OF THE INVENTION

The present invention discloses a device for directionally placing a plant propagule inside a hollow member, as well as a method for growing a root from a plant propagule (2) inside a hollow member (3).

The present invention relates to the following items. The subject matter disclosed in the items below should be regarded disclosed in the same manner as if the subject matter were disclosed in patent claims.

1. A device for directionally placing a plant propagule (2) inside a hollow member (3), comprising:
    a. a platform element arranged (20) such that a foldable member (1) can be placed thereon;
    b. an actuating dispensing arrangement (90a, 90b, 100) for placing a foldable member (1) on the platform element (20);
    c. an arrangement (40, 50, 57)/(40a) for placing a plant propagule (2) on a foldable member (1) placed on the platform element (20);
    d. optionally, means (150) for identifying an imaginary line (9) on the foldable member (1) stretching through the root forming end (7) to the shoot forming end (8) of the plant propagule (2) being directionally placed during operation;
    e. an actuating folding arrangement (30, 80)/(120/80) for folding the foldable member (1) along said imaginary line (9) to form a folded foldable member (1a);
    f. an actuating dispensing arrangement (180) for providing a hollow member (3) having a first open end (4); and g. an actuating placing arrangement (30, 80)/(120/80) for placing said folded foldable member (1*a*) into the hollow member (3) through the first open end (4);

wherein the device is configured for performing a method for directionally placing a plant propagule (2) inside a hollow member (3), such that during operation, the device performs the steps of:

I. providing a hollow member (3) having a first open end (4) by means of an actuating dispensing arrangement (180);

II. providing a foldable member (1), and placing it on the platform element (20);

III. placing a plant propagule (2) on said foldable member (1) placed on the platform element (20);

IV. optionally, identifying the root forming end (7) and the shoot forming end (8) of the plant propagule (2) and identifying an imaginary line (9) across the foldable member (1) stretching through the root forming end (7) to the shoot forming end (8) of the propagule (2), by the means (150) for identifying an imaginary line (9));

V. folding the foldable member (1) along said line (9) by means of the actuating folding arrangement (30, 80)/(120/80) such that the plant propagule (2) becomes wrapped in the folded foldable member (1*a*); and VI. placing said folded foldable member (1*a*) with the wrapped plant propagule (2) into the hollow member (3) through the first open end (4) by means of the actuating placing arrangement (30, 80)/(120/80).

2. The device according to any of the preceding items, wherein the platform element (20) is rotatable along an axis (22).

3. The device according to any of the preceding items, wherein the platform element (20) is arranged on a support element (10) rotatable along an axis (12).

4. The device according to any of the preceding items, comprising four or more platform elements.

5. The device according to any of the preceding items, wherein the actuating dispensing arrangement (90*a*, 90*b*, 100) for placing a foldable member (1) on the platform element (20) comprises a suction device (105) placed on an actuator (100) wherein the suction device (105) is configured for picking up a foldable member (1) and placing it on top of the platform element (20) during operation.

6. The device according to any of the preceding items, wherein the arrangement (40) for placing a plant propagule (2) on a foldable member (1) placed on the platform element (20) comprises:
a. a delivery conduit (40) capable of delivering a stream of fluid comprising plant propagules (2) suspended in the fluid, wherein the delivery conduit (40) is located above the platform element (20);
b. a collection conduit (50) capable of collecting the stream of fluid;
c. a detector (140) for detecting a plant propagule (2) in the stream of fluid in the delivery conduit (40);
d. an actuating means (57) for reversibly diverting the collection conduit (50) when a plant propagule (2) is detected, operatively connected to the detector (140) for detecting a plant propagule (2);

wherein the device is configured such that in operation, the actuating dispensing arrangement (90*a*, 90*b*, 100) for placing a foldable member (1) on the platform element (20) places a foldable member (1) on the platform element (20); and when a plant propagule (2) is detected in the stream of fluid in the delivery conduit (40), the actuating means (57) for diverting the collection conduit (50) is activated by the detector (140) for detecting a plant propagule (2) such that the stream of fluid from the delivery conduit (40) places the plant propagule (2) on the foldable member (1), after which the diversion of the collection conduit (50) is reverted by the actuating means (57) in preparation of the next propagule.

7. The device according to any of items 1-5, wherein the arrangement (40*a*) for placing a plant propagule (2) on a foldable member (1) placed on the platform element (20) comprises:
a conduit (40*a*) having a first outlet (41) and a second outlet (42) capable of delivering a stream of fluid comprising plant propagules (2) suspended in the fluid, wherein the second outlet (42) of the conduit (40*a*) is located above the platform element (20), and wherein the first outlet (41) is arranged such that it may be provided with interruptible suction during operation; and
a detector (140) for detecting a plant propagule (2) in the stream of fluid in the conduit (40*a*);
wherein the device is configured such that during operation, the actuating dispensing arrangement (90*a*, 90*b*, 100) for placing a foldable member (1) on the platform element (20) places a foldable member (1) on the platform element (20);
in a default state, the first outlet (41) is provided with a suction such that the stream of fluid (52) is prevented from exiting through the second outlet (42); and
when a plant propagule (2) is detected in the stream of fluid in the delivery conduit (40*a*), the suction through the first outlet (41) is interrupted for such time that the plant propagule (2) exits through the second outlet (42) with the stream of fluid and becomes placed onto the foldable member (1), after which the suction through the first outlet (41) is resumed.

8. The device according to any of the preceding items, wherein the actuating folding arrangement (30,80) for folding the foldable member along said imaginary line (9) comprises a sliding linear actuator (80) and a folding platform (30) for a foldable member (1).

9. The device according to any of the preceding items, wherein said means (150) for identifying an imaginary line (9) on the foldable member (1) comprises a digital imaging arrangement (150) for identifying the root forming end (7) and the shoot forming end (8) of the plant propagule (2) and for identifying an imaginary line (9) on the foldable member (1) stretching through the root forming end (7) to the shoot forming end (8) of the propagule (2).

10. The device according to any of the preceding items, wherein the actuating dispensing arrangement (180) for providing a hollow member (3) comprises linear actuators (190) with capability to move in different directions during operation.

11. The device according to any of the preceding items, wherein the actuating placing arrangement (80,120) for placing said folded foldable member (1*a*) into the hollow member (3) through the first open end (4) such that the root forming end (7) of the propagule (2) is directed away from the first end (4) of said hollow member (3) comprises of a gripping and sliding actuation mechanism (120) and a sliding linear actuator (80), wherein the device is configured such that during operation, the following steps are performed by the device:
a. The actuator (80) is moved to become located on top of the foldable member (1) with a propagule (2) (FIG. 7A, 7B);
b. The mechanism (120) is moved to fold the foldable member (1) along the imaginary line (9) (FIG. 7C, 7D);
c. The folded foldable member (1a) is held in place by actuator (80) and mechanism (120) which move the folded foldable member (1a) into a hollow member (3), after which the actuator (80) is lifted (FIG. 7E) and mechanism (120) disengaged thereby placing the folded foldable member (1a) in the hollow member (3).

12. The device according to any of the preceding items, wherein the actuating folding arrangement (80,120)/(30,80) is configured to also function as an actuating placing arrangement.

13. The device according to any of the preceding items, comprising means (150) for identifying an imaginary line (9) on the foldable member (1) stretching through the root forming end (7) to the shoot forming end (8) of the plant propagule (2) being directionally placed during operation, and being configured such that during operation it performs identifying the root forming end (7) and the shoot forming end (8) of the plant propagule (2) and identifying an imaginary line (9) across the foldable member (1) stretching through the root forming end (7) to the shoot forming end (8) of the propagule (2), by the means (150) for identifying an imaginary line (9)).

14. A method for growing a root from a plant propagule (2) inside a hollow member (3) comprising the steps of:
a. providing a hollow member (3) having a first open end (4);
b. providing a foldable member (1);
c. placing a plant propagule (2) on said foldable member (1);
d. identifying the root forming end (7) and the shoot forming end (8) of the plant propagule (2);
e. identifying an imaginary line (9) across the foldable member (1) stretching through the root forming end (7) to the shoot forming end (8) of the plant propagule (2);
f. folding the foldable member (1) along said line (9) such that the plant propagule (2) is wrapped in the folded foldable member (1a);
g. placing said folded foldable member (1a) with the wrapped plant propagule (2) into the hollow member (3) through the first open end (4);
h. providing a suitable growth medium to the wrapped plant propagule (2);
i. incubating the wrapped plant propagule (2) in suitable conditions and for a sufficient time for a root to form, whereby a root is formed inside said hollow member (3);
wherein the method steps a-g are carried out with a device according to any of items 1-13.

15. The method according to any of the preceding method items, wherein the step (g) of placing said folded foldable member (1a) with the wrapped plant propagule (2) into the hollow member (3) through the first open end (4) further comprises placing the folded foldable member (1a) such that the root forming end (7) of the propagule (2) is directed away from the first end (4) of said hollow member (3).

16. The method according to any of the preceding method items, wherein the hollow member (3) is elongated having a second end and is tapered such that it has a smaller cross-sectional area at the second end compared to the first end (4).

17. The method according to any of the preceding method items, wherein the hollow member (3) is open at the second end.

18. The method according to any of the preceding method items, wherein the hollow member (3) has a tubular shape.

19. The method according to any of the preceding method items, wherein the hollow member (3) comprises a notch or a slot at the first end.

20. The method according to any of the preceding method items, wherein the hollow member (3) is formed by wrapping a sheet thus forming a hollow member (3).

21. The method according to any of the preceding method items, wherein the foldable member (1) comprises paper and/or a flexible plastic material.

22. The method according to any of the preceding method items, wherein the plant propagule (2) is placed at the center region of the foldable member (1).

23. The method according to any of the preceding method items, wherein the plant propagule (2) is placed on the foldable member (1) by means of a fluid stream.

24. The method according to any of the preceding method items, wherein the growth medium in step (h) is in liquid form.

25. The method according to any of the preceding method items, wherein the plant propagule (2) is a plant tissue fragment, a plant callus fragment, a plant somatic embryo or any other root forming unit.

26. The method according to any of the preceding method items, wherein the plant propagule (2) is a somatic embryo.

27. The method according to any of the preceding method items, wherein the plant propagule (2) is a conifer somatic embryo.

28. The method according to any of the preceding method items, wherein the plant propagule (2) is a spruce somatic embryo.

29. The method according to any of the preceding method items, wherein the plant propagule (2) is a Norway spruce somatic embryo.

30. The method according to any of items 28-29, wherein the suitable conditions in step (i) comprise placing the plant propagule (2) under light at 18-22 degrees Celsius.

31. The method according to any of the preceding method items, further comprising the step (j) of planting the plant propagule (2) in a solid growth substrate, manually or by means of an automated planting system.

BRIEF DESCRIPTION OF THE DRAWINGS

In the drawings, the reference signs have the meanings indicated in the following table. Details concerning the elements are further explained in the detailed description.

EXPLANATIONS OF REFERENCE SIGNS

Figure 4:
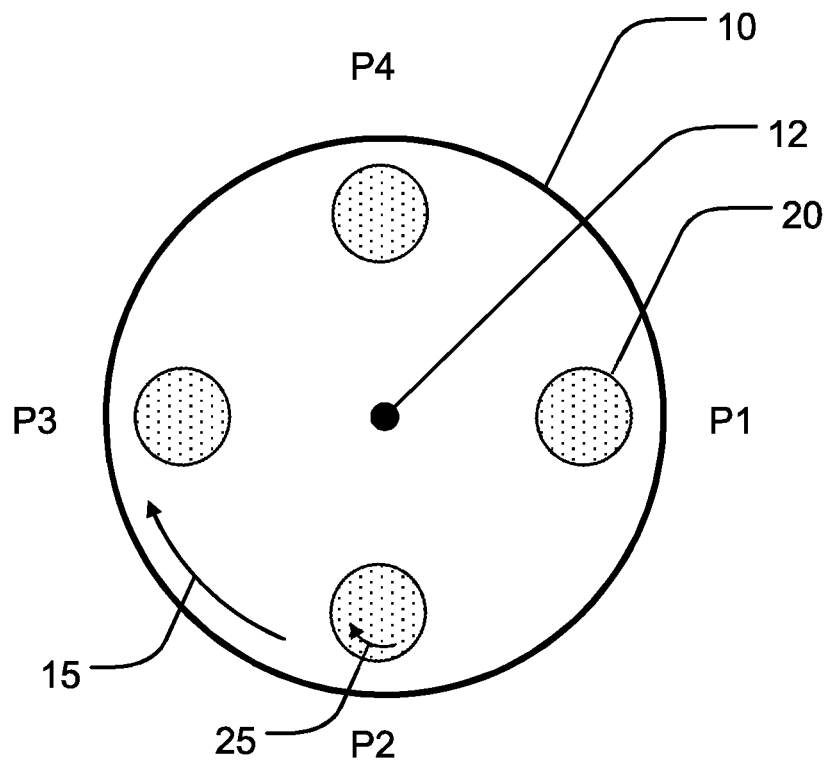
Figure 4:
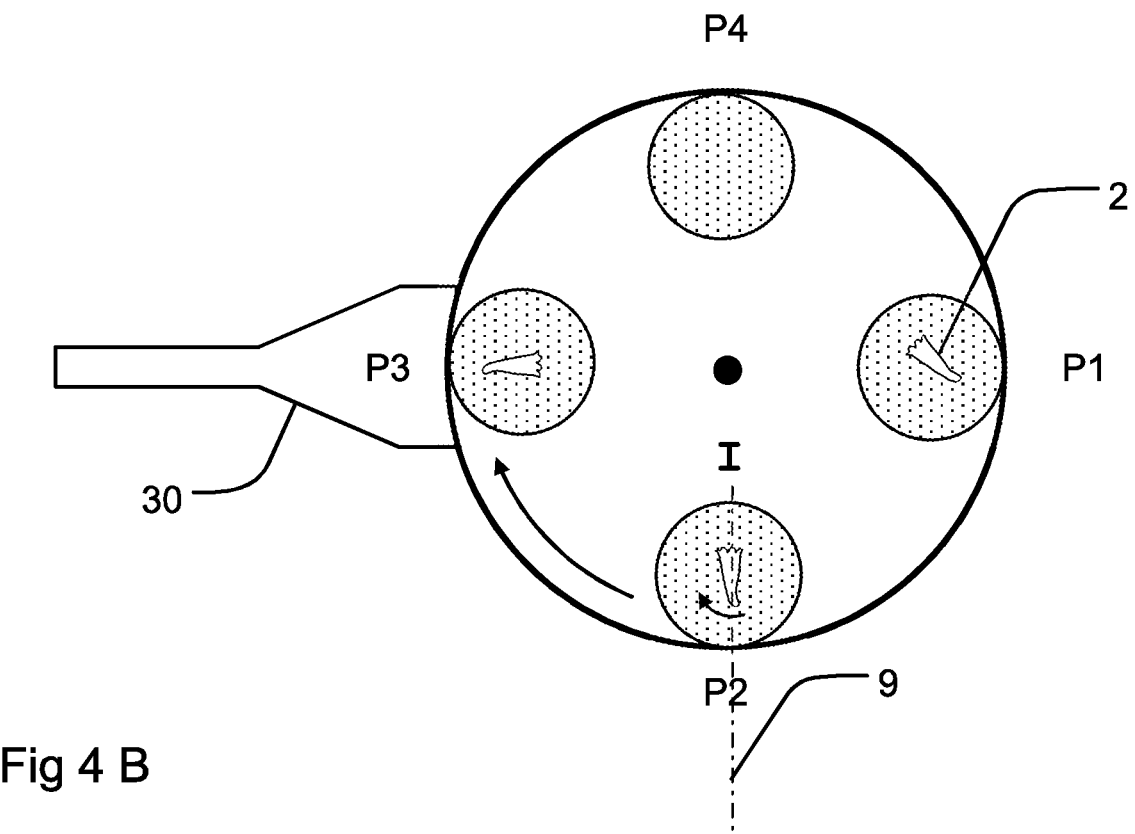
Figure 4:
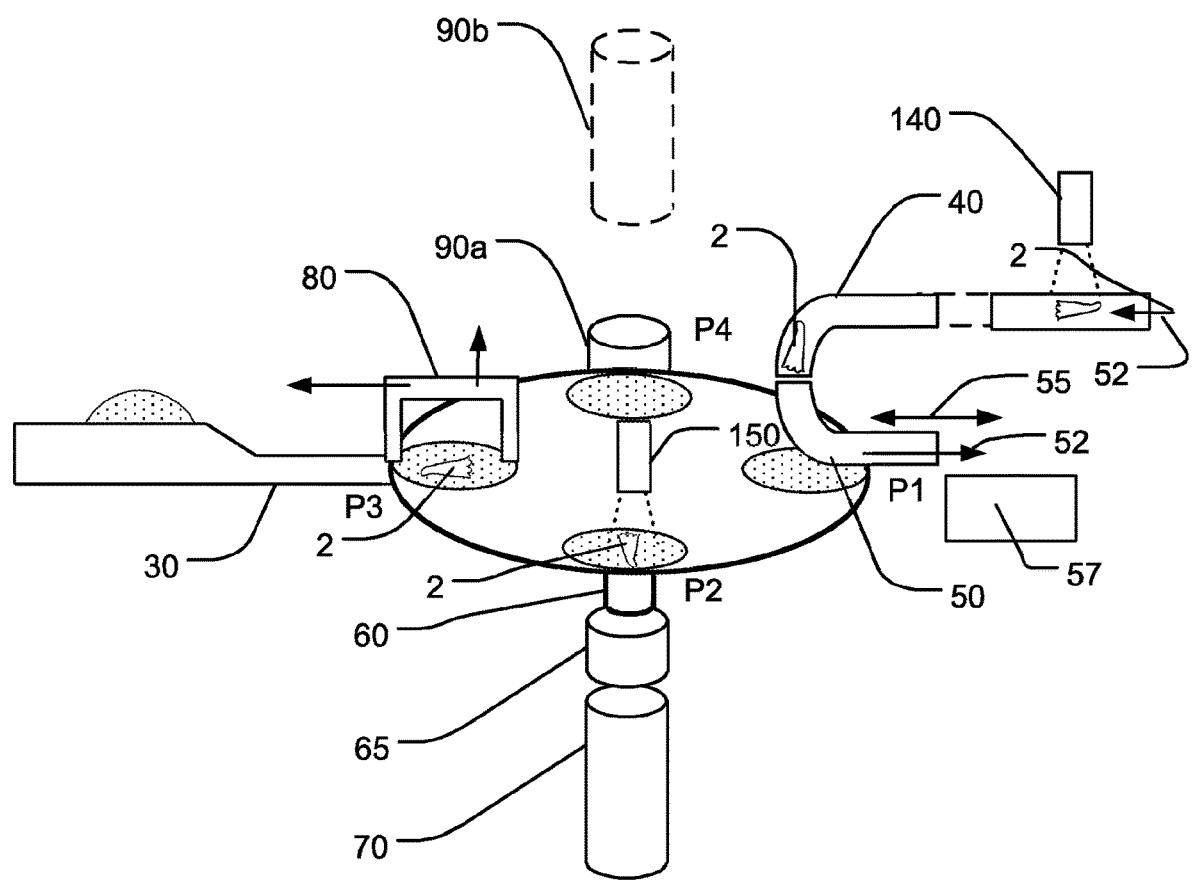
Figure 4:
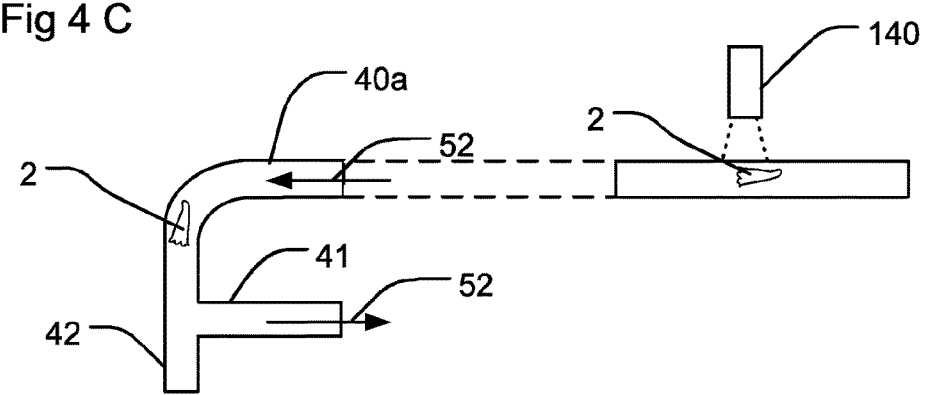

| Sign | Explanation |
|---|---|
| P1 | Position of platform element (20) for placing a plant propagule (2) |
| P2 | Position of platform element (20) for identification of the root forming end (7) and the shoot forming end (8) of the plant propagule (2) |
| P3 | Position of platform element (20) for folding the foldable member (1) |
| P4 | Position of platform element (20) for receiving a new foldable member (1) being provided |
| 1 | Foldable member |
| 1a | Foldable member, folded |
| 2 | Plant propagule |
| 3 | Hollow member |
| 4 | First open end of the hollow member (3), with notch |
| 5 | Arrow O-A indicating orientation of the plant propagule (2) with the shoot forming end (8) in the direction of the arrow, and the root forming end (7) in the opposite direction of the arrow |
| 6 | Second end of the hollow member (3) |
| 7 | Root forming end of the propagule (2) |
| 7a | Root forming end of the propagule (2) shown with root |
| 8 | Shoot forming end of the propagule (2) |
| 8a | Shoot forming end of the propagule (2) shown with shoot |
| 9 | Imaginary line on the foldable member stretching through the root forming end (7) to the shoot forming end (8) of the propagule (2) |
| 10 | Support element for a platform element, shown as a discoidal support with four platform elements |
| 12 | Rotation axis for support element (10) |
| 15, 15a | Rotation indication of the discoidal support element (10), both directions possible |
| 20 | Platform element |
| 22 | Axis of rotation for platform element (20) |
| 25 | Rotation indication for platform element (20) at position P2, where the foldable member (1) with propagule (2) may be rotated to align with the folding arrangement (30, 80)/(80, 120) |
| 30 | Folding platform component of the folding arrangement |
| 30a | Detail view of a folding platform component of the folding arrangement, top view |
| 30b | Detail view of a folding platform component of the folding arrangement, view from broader end |
| 30c | Detail view of a folding platform component of the folding arrangement, view from narrower end |
| 30d | Detail view of a folding platform component of the folding arrangement, side view |
| 40 | Arrangement for placing a plant propagule (2) on a foldable member (1) placed on the platform element (20), depicted as conduit embodiment in drawings |
| 40a | Arrangement for placing a plant propagule (2) on a foldable member (1) placed on the platform element (20), alternative embodiment, no moving parts and less volume of solution is placed in the foldable member (1). Depicted as an alternative conduit in drawings. |
| 41 | First outlet of a conduit (40a) |
| 42 | Second outlet of a conduit (40a) |
| 50 | Collection conduit (50) capable of collecting the stream of fluid; |
| 52 | Indication of fluid flow direction in the conduits (40) and (50) |
| 55 | Indication of motion of collection conduit (50) during operation |
| 57 | Actuating means for reversibly diverting the collection conduit (50) |
| 60 | Alignment means for enabling alignment of foldable member (1) with the plant propagule (2) to be rotated to align with the folding arrangement (30, 80)/(80, 120) |
| 65 | Optional connector between alignment means (60) and motor (70) |
| 70 | Motor/step motor for rotating position P2 |
| 80 | Actuating placing arrangement for placing a folded foldable member (1a) into the hollow member (3), movable in two directions. May also function as part of the folding arrangement component together with a folding platform (30) or a gripping and sliding actuation mechanism (120). |
| 90a | Stack holder for new foldable member |
| 90b | Stack holder for new foldable member, optionally placed above P4 |
| 100 | Actuating dispensing arrangement for placing a foldable member (1) on the platform element (20), illustrated here implemented as a robot arm |
| 105 | Suction device configured for picking up the foldable member (1) |
| 110 | Support for the foldable member (1) to rest on |
| 115 | Tubular member for providing low pressure to keep the foldable member in fixed position when on supports (110) in positions P1-P4 |
| 117 | Tubular means for providing low pressure to tubular member (115) |
| 120 | Gripping and sliding actuation mechanism for folding the foldable member (1) |
| 130 | Rack for storage of the tubular members (3) with folded foldable members (1a) with plant propagules (2) |
| 140 | Detector for detecting a plant propagule (2) in the stream of fluid in the delivery conduit (40a); |
| 150 | Means (150) for identifying an imaginary line (9) on the foldable member (1) stretching through the root forming end (7) to the shoot forming end (8) of the plant propagule (2) |
| 160 | Container for growth medium or substrate |
| 170 | Growth medium or substrate |
| 180 | Actuating dispensing arrangement for providing a hollow member (3) |
| 190 | Linear actuators of the dispensing arrangement (180) with capability to move in different directions during operation |

FIG. 1a depicts a folded foldable member (1a).

FIGS. 1b and 1c depict two types of plant propagule (2) (1b: somatic embryo; 1c a cutting), each with a root forming end (7) and a shoot forming end (8).

FIG. 1d depicts a foldable member (1) (in unfolded state) with a plant propagule (2), in this case a mature somatic embryo (2) positioned on the foldable member (1) with an imaginary line (9) on the foldable member (1) stretching through the root forming end (7) to the shoot forming end (8) of the plant propagule (2).

The arrow O-A (5) in FIGS. 1bcd, pointing from O to A indicates orientation of the plant propagule (2) with the shoot forming end (8) in the direction of the arrow, and the root forming end (7) in the opposite direction of the arrow.

FIG. 2 depicts a tubular hollow member (3) with a first open end (4) provided with a slot.

FIG. 3a depicts the foldable member (1) folded along the axial direction of the plant propagule where the plant propagule (2) and the folded foldable member are placed in the slot at the first open end (4) of the tubular hollow member (3) such that the shoot forming end (8) sticks out from the tubular hollow member and the root forming end (7) points into the hollow member.

FIG. 3b depicts the plant propagule after germination and root formation where the root (7a) has naturally grown from the root forming end inside the hollow member (hatched) and the shoot grown off the shoot forming end (8a) sticks outside of the hollow member.

FIG. 4A shows a schematic top view of support element (10) for platform elements (20) with a rotation indication (15) (both directions are possible) around rotation axis (12). Platform elements (20) located at positions P1-P4. Each position P1-P4 is configured for performing a specific stage in the propagule handling process: position P1 for placing a plant propagule (2) on a foldable member (1), position P2 for aligning the propagule (2) with the folding arrangement (30,80)/(80,120), position P3 for folding the foldable member (1); and position P4 for providing a new foldable member (1).

FIG. 4B shows a schematic top view of a support element (10) with platform elements (29). A plant propagule (2) i shown on a foldable member (1) on platform element at position P1, a plant propagule (2) on a foldable member (1) rotated at position P2 as to align the root forming end (7) to the shoot forming end (8) of the plant propagule with an imaginary line (9). Also shown is an aligned a plant propagule (2) on a foldable member (1) next to the folding platform component (30) of the folding arrangement at position P3.

FIG. 4C shows a 3D side view of a device for directionally placing a plant propagule (2) inside a hollow member (3). The device comprises an arrangement (40) at position P1 for placing a plant propagule (2) on the foldable member (1) (shown as dotted circles).

Also shown are means (150) for identifying an imaginary line (9) on the foldable member (1) stretching through the root forming end (7) to the shoot forming end (8) comprising a means for imaging (150) and alignment means (60) at position P2.

Also indicated is an actuating dispensing arrangement (180) for providing a hollow member (3) (not shown in detail) and an actuating folding arrangement (30,80) in position P3 for folding the foldable member (1) along said imaginary line (9), with an actuating placing arrangement (80) for placing the foldable member (1) into the hollow member (3). Position P4 is for providing a new foldable member (1) from dispensing arrangement (90a, 90b).

FIG. 4D shows an arrangement for placing a plant propagule (2) on a foldable member (1) (not shown), comprising a delivery conduit (40a) capable of delivering a stream of fluid comprising plant propagules (2) suspended in the fluid, and a detector (140) for detecting a plant propagule (2) in the stream of fluid in the delivery conduit (40a).

Figure 5A:
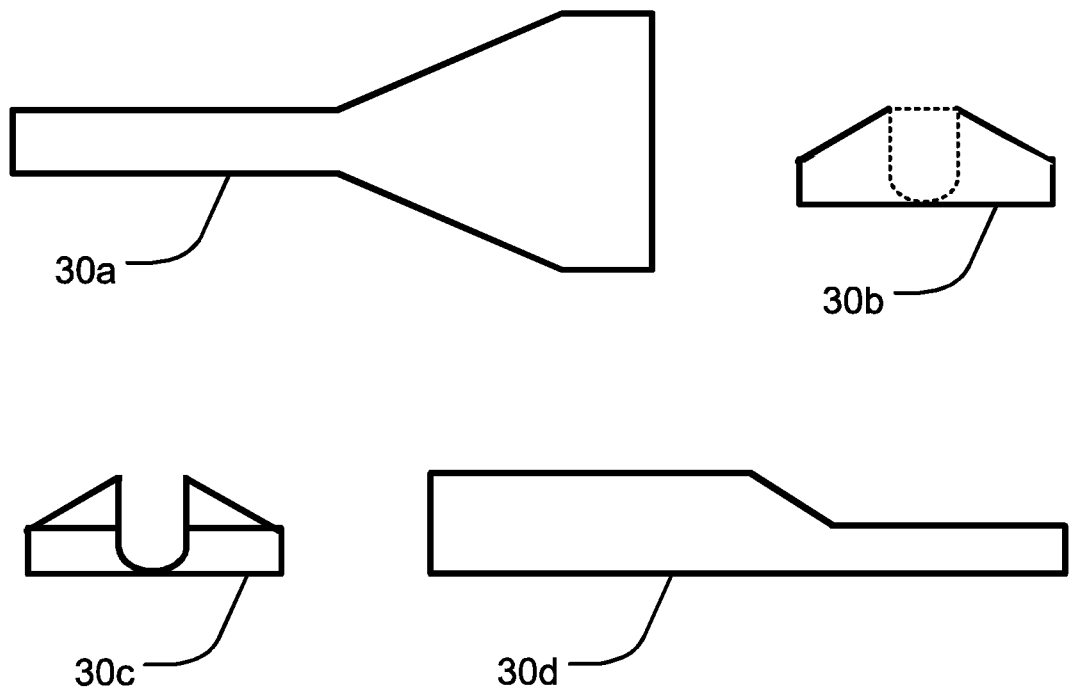

FIG. 5a illustrates the folding device for folding the foldable member from different angles. Top view of the folding platform (30a). The folding platform (30b) as viewed towards the platform element (20). The folding platform (30c) as viewed from the platform element (20) showing a slot for holding the hollow member (3). Side view of the folding platform (30d).

Figure 5B:
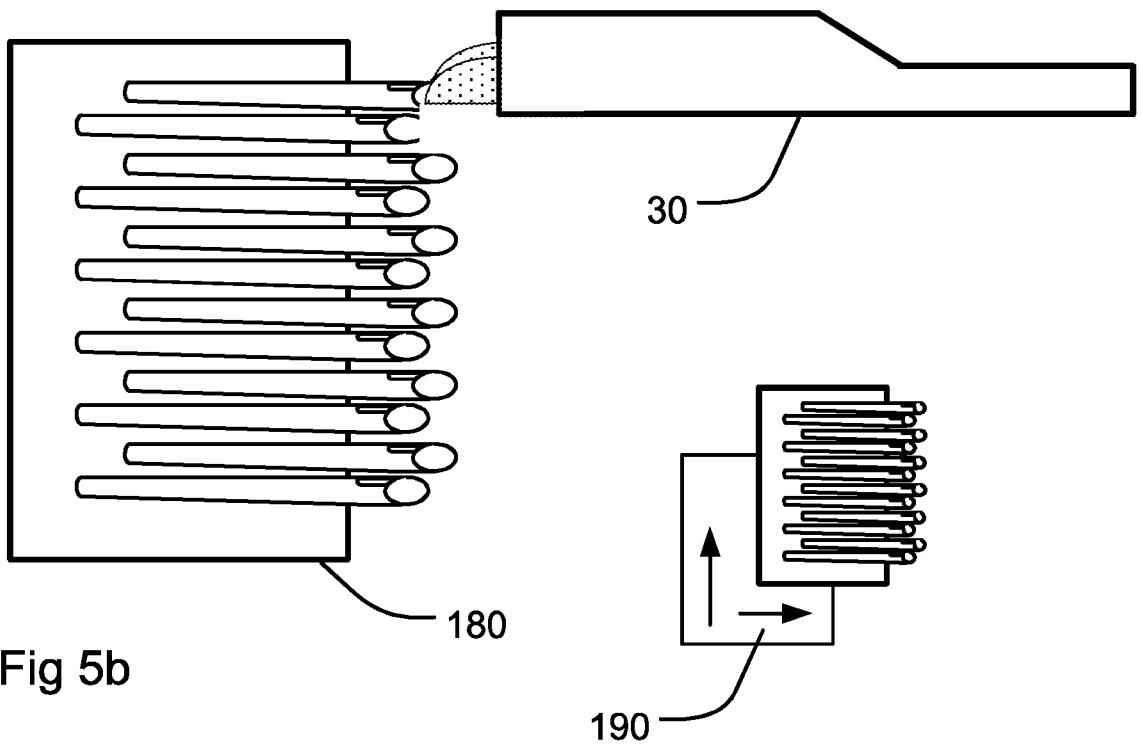

FIG. 5b depicts an actuating dispensing arrangement (180) for providing a hollow member (3). The folded foldable members (1a) can be inserted into the hollow members (3) entering through the folding platform (30). Also shown are linear actuators (190) of the dispensing arrangement (180) with capability to move in different directions during operation (arrows).

Figure 6:
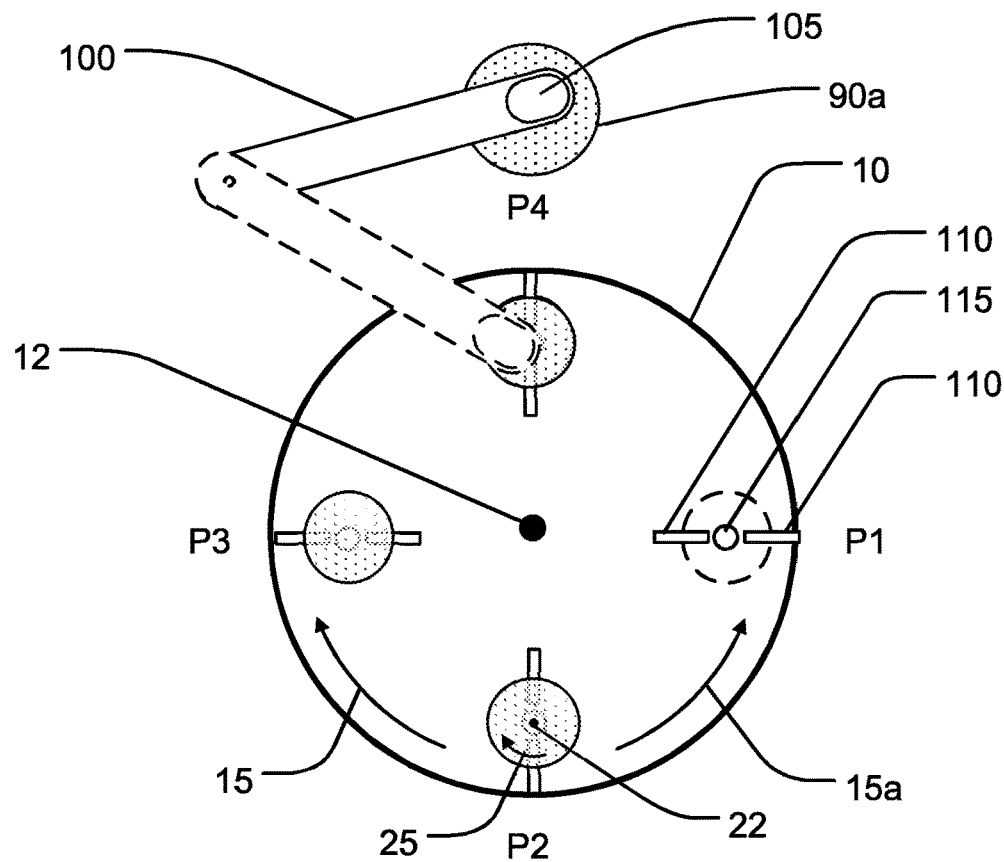
Figure 6:
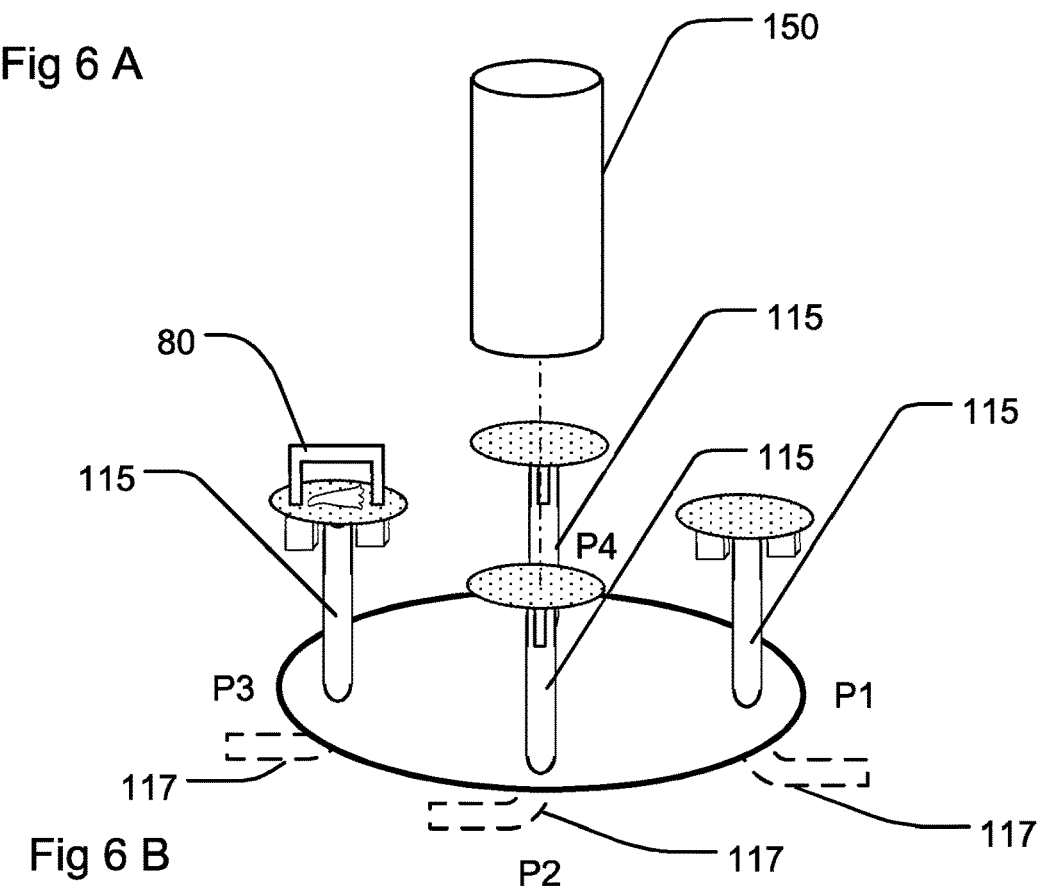
Figure 7:
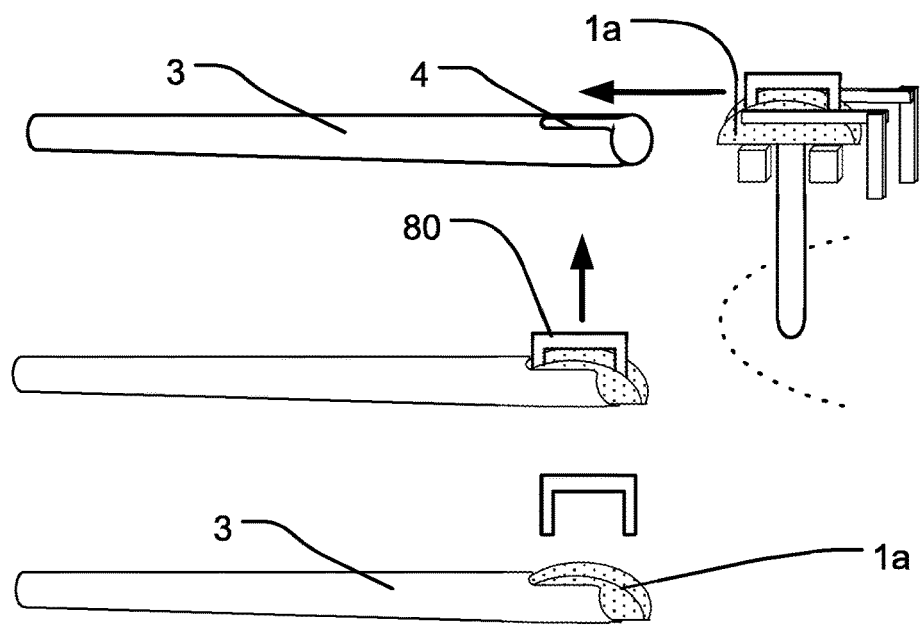
Figure 7:
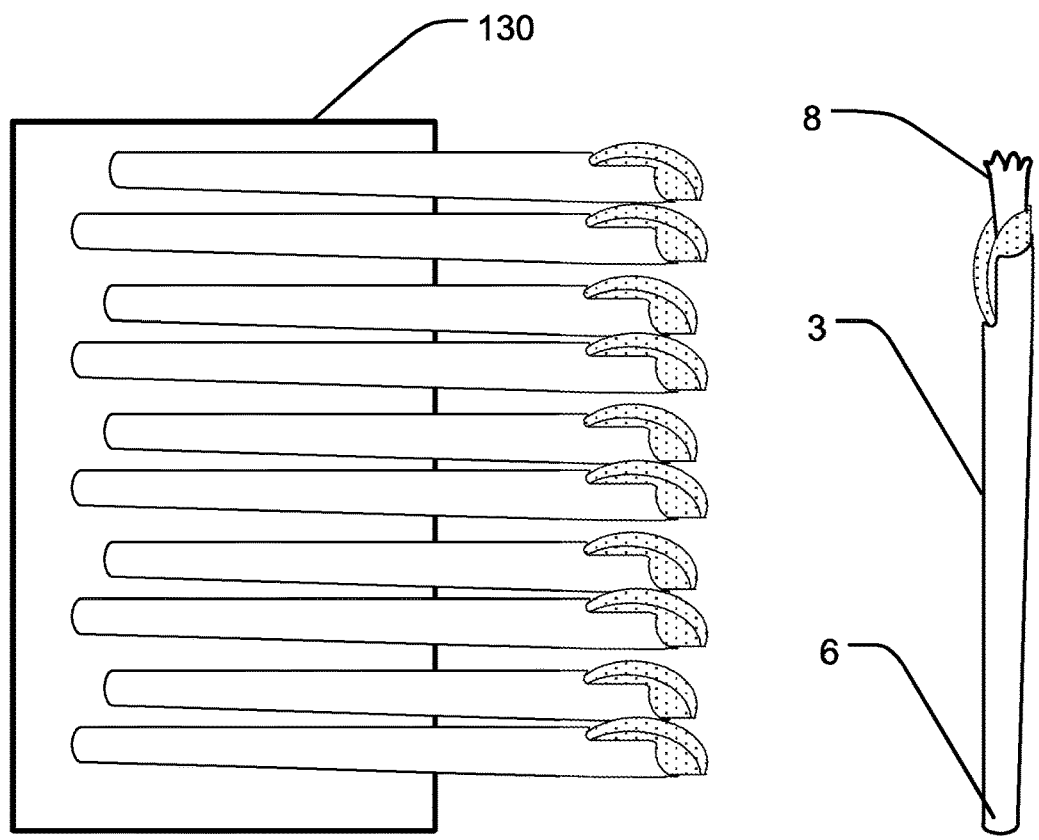
Figure 7:
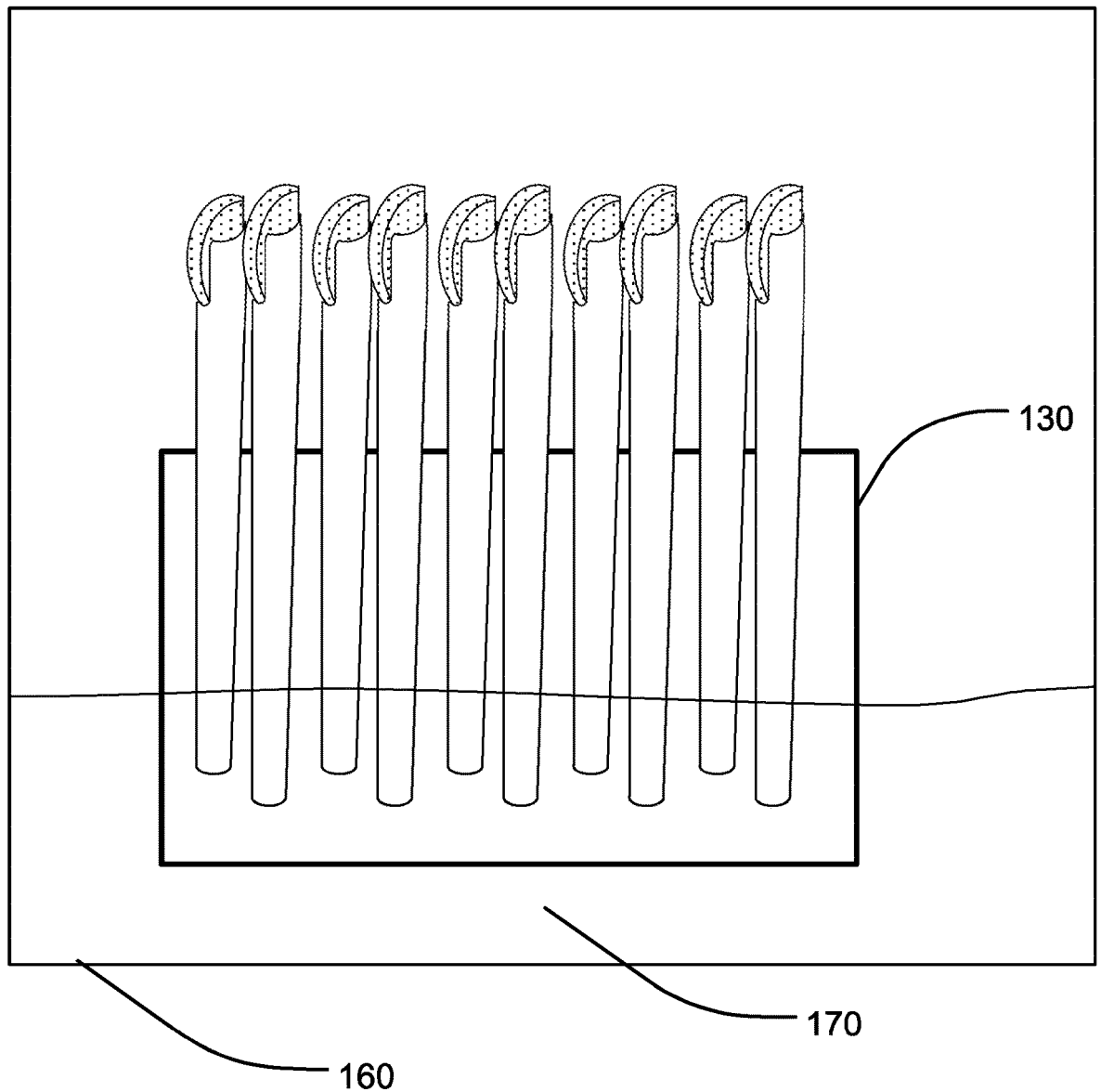

FIG. 6A illustrates a top view of a platform element (20) comprising a suction device (105) placed on an actuator (100) for picking up the foldable member (1) from a stack holder (90a) for new foldable members, a support (110) for supporting the foldable member (1), a tubular member (115) with low pressure to keep the foldable member (1) in a fixed position.

FIG. 6B illustrates a 3D side view of an alternative configuration of the platform element (20) with a means (150) for identifying an imaginary line (9) on a foldable member (1), and an actuating placing arrangement (80) for placing the foldable member (1) into the hollow member (3). The positions P1-P4 are supported by tubular members (115) provided during operation with low pressure through tubular means (117) to keep the foldable member (1) in a fixed position.

FIGS. 7A-E illustrate in detail an embodiment combining the functions of the actuating folding arrangement and the actuating placing arrangement in a single arrangement.

FIG. 7F illustrates a rack (130) for storage of a plurality of hollow members (3) with folded foldable members with propagules (not shown).

FIG. 7G illustrates a rack (130) with a plurality of hollow members (3) with folded foldable members with propagules (not shown) placed for growth in a container (160) with growth substrate (170).

Figure 8:
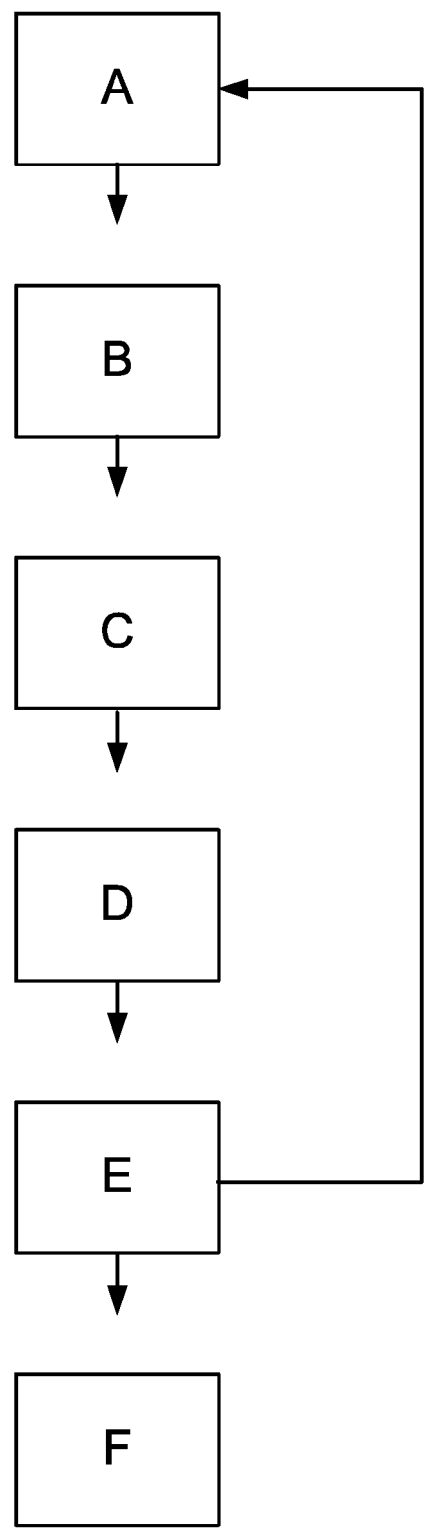

FIG. 8: Flow chart of the operation of the device and the method of the invention. Stages A-E, as illustrated in FIG. 8, may be performed by the device of the invention.

Stage A: Provide a hollow member (3) having a first open end (4) and a foldable member (1).

Stage B: Place a plant propagule (2) on the foldable member (1).

Stage C: identify the root forming end (7) and the shoot forming end (8) of the plant propagule (2) and subsequently identify an imaginary line (9) across the foldable member (1) stretching through the root forming end (7) to the shoot forming end (8).

Stage D: Fold the foldable member (1) along said imaginary line (9) such that the plant propagule (2) is wrapped in the foldable member (1).

Stage E: Place said folded foldable member (1a) with the wrapped plant propagule (2) into the hollow member (3) through the first open end (4); The arrow from E back to A illustrates that the device may begin processing the next plant propagule.

Stage F: Provide a suitable growth medium to the wrapped plant propagule (2), and incubate the wrapped plant propagule (2) in suitable conditions and for a sufficient time for a root to form, whereby a root is formed inside said hollow member (3).

DETAILED DESCRIPTION

A Method for Growing a Root from a Plant Propagule Inside a Hollow Member

In a first aspect, the present invention provides a method for growing a root from a plant propagule (2) inside a hollow member (3) comprising the steps of:
  a) providing a hollow member (3) having a first open end (4);
  b) providing a foldable member (1);
  c) placing a plant propagule (2) on said foldable member (1);
  d) if necessary, identifying the root forming end (7) and the shoot forming end (8) of the plant propagule (2);
  e) if necessary, identifying an imaginary line (9) across the foldable member (1) stretching through the root forming end (7) to the shoot forming end (8) of the propagule;
  f) folding the foldable member (1) along said line such that the plant propagule (2) is wrapped in the folded foldable member (1a);
  g) placing said folded foldable member (1a) with the wrapped plant propagule (2) into the hollow member (3) through the first open end (4);
  h) providing a suitable growth medium to the wrapped plant propagule (2);
  i) incubating the wrapped plant propagule (2) in suitable conditions and for a sufficient time for a root to form, whereby a root is formed inside said hollow member (3).

Certain types of plant propagules (2) display a strong tendency for the root to grow downwards in the direction of the gravitational pull, whereas for other types of plant propagules (2) (such as conifer somatic embryos), gravity has little or no effect. In particular, in cases where the gravitational pull has a significant effect on the plant propagule (2), the method may further comprise the step g' of placing the hollow member (3) with the wrapped plant propagule (2) such that the root forming end (7) is directed in a downward direction, prior to the incubation step, to ensure that the root grows in the desired direction.

The step of placing said folded foldable member (1a) with the wrapped plant propagule (2) into the hollow member (3) through the first open end (4) may further comprise placing the folded foldable member (1a) such that the root forming end (7) of the propagule is directed away from the first end (4) of said hollow member (3). In preferable embodiments, the hollow member (3) is substantially longer than the wrapped propagule (2) placed into it, and the wrapped propagule (2) is placed at the first open end (4). Thus, the propagule is preferably placed such that the root may grow into the cavity within the hollow member (3) in the direction away from the first open end (4). It is also conceivable however for some applications that the propagule be placed with the root growing in the direction of the first open end (4).

The steps of the method as preferably performed sequentially in the alphabetical order presented here but this is not necessarily the case.

Types of Plant Propagules (2)

In the method of the first aspect, the plant propagule (2) may be a plant tissue fragment, a plant callus fragment, a plant somatic embryo or any other root forming unit. (see FIG. 1b-c)

Preferably, the plant propagule (2) is a somatic embryo. More preferably, the plant propagule (2) is a conifer somatic embryo. Even more preferably, the plant propagule (2) is a spruce somatic embryo. Most preferably, the plant propagule (2) is a Norway spruce somatic embryo.

Hollow Member (3) Referred to in (a)

The hollow member (3) is arranged to be suitable for placing a plant propagule (2) wrapped in the foldable member (1) as described below.

The hollow member (3) may be elongated having a second end (6). It may preferably be tapered such that it has a smaller cross-sectional area at the second end (6) compared to the first end (4). The hollow member (3) may be open at the second end (6).

These arrangements provide certain advantages in the subsequent handling, in particular in subsequent planting of a propagule (2) using the method and/or device of PCT/IB2014/067084. An advantage of a tapered hollow member (3) with an open second end (6) is that the member can penetrate the substrate (peat moss or any other soil) more easily and any water or liquid media can drain from the member (3). Also an open second end (6) will allow air circulation which in some cases may be important.

The hollow member (3) may have a tubular shape such as an elongated open-ended tube. The cross-section may have any shape compatible with the application, such as circular, oval, triangular, square, rectangular, pentagonal and octagonal or the like. In most applications, a substantially circular cross-section is preferable from a practical point of view.

Preferably, the hollow member (3) comprises a notch, a slit or a slot at the first end (4) (see FIG. 2). This facilitates the subsequent step of placing a wrapped propagule (2) into the hollow member (3). A slit at the first end (4) will allow a foldable member (1) with a folded radius larger than the diameter of the hollow member (3) to be held in place inside the hollow member (3). Part of the folded foldable member (1a) will in this case remain outside of the hollow member (3), as shown in the FIG. 3a-b.

The notch, slit or slot may be formed as a mechanism to hold the folded foldable member (1a) wrapping the propagule (2) in place. This arrangement also has the advantage of ensuring the proper planting of the rooted propagule in a substrate without the shoot being dragged into the substrate. Preferably, the hollow member (3) is substantially of biodegradable material. The hollow member (3) may be formed by wrapping a sheet of a suitable material to form a hollow tube. For example, the hollow member (3) could be of rolled paper.

Foldable Member (1) Referred to in (b)

The foldable member (1) is arranged to be suitable for wrapping a plant propagule (2) in the foldable member (1), and for subsequent placing of the wrapped plant propagule (2) in the hollow member (3) described above (see FIGS. 1-3). Thus, the dimensions of the hollow member (3) and the foldable member (1) are chosen such that they are mutually compatible for their intended purpose and of suitable size with regard to the plant propagule (2) being handled.

The foldable member (1) may be formed by cutting an e.g. circular section of a filter paper or any other foldable material. The member can be folded wrapping the propagule in different ways. One mechanism is manually with the aid of forceps. By holding the foldable member (1) about 180 degrees apart, two positions on its edge(s) can be folded against each other in a symmetric shape resulting in the foldable member (1) wrapping around the plant propagule (2) as shown in FIG. 3. Another mechanism of folding the foldable member (1) is by automating the process as shown and explained in FIGS. 4-7.

The foldable member (1) may comprise paper and/or a flexible plastic material, or the like. An advantage with paper is that paper can remain in soil in which the propagule is later planted without any harm to the environment as it is biodegradable. Biodegradable materials are generally preferred for the folded member for this reason. The foldable member (1) may comprise a sheet, a mesh, a nonwowen or a net, or a combination thereof, or the like. It is preferable that the foldable member (1) is water-permeable, e.g. perforated or sufficiently porous enabling placement of a plant propagule (2) carried with a fluid such as water. This feature is particularly important and useful in certain automation processes where the propagule is placed on the surface of the member by carrying the propagule in a liquid jet, as shown in FIGS. 4C-D.

The foldable member (1) may have in principle any suitable shape, such as circular, oval, triangular, square, rectangular, pentagonal and octagonal or the like. A substantially circular foldable member (1) is preferred. For instance, the foldable member (1) could be a substantially circular sheet of filter paper. Alternatively, the foldable member (1) could be a circular or rectangular sheet of pliable plastic mesh or a non-woven fabric.

The foldable member (1) may be of any colour. A darker colour is preferred and a black foldable member (1) is most preferred. The advantage with a dark foldable member (1) is that it simplifies the imaging of the propagule when the imaginary line (9) is determined, such as with means (150).

Placing a Plant Propagule (2) on the Foldable Member (1) (Step c)

Preferably, the plant propagule (2) is placed at the center region of the foldable member (1). The placing the plant propagule (2) may be carried out in any manner, including manual placement, placement by means of a robotic arm, placement by means of a carrier liquid or air stream and the like. A suitable placement means is disclosed in WO2011/042888.

Preferably, the plant propagule (2) is placed on the foldable member (1) by means of a fluid stream (see FIGS. 4C-D), as this allows convenient continuous delivery of plant propagules (2) with minimal physical stress to the propagules. The fluid can e.g. be water or a plant-compatible buffer. The plant propagules (2) may be suspended in the fluid and carried to the foldable member (1) in a stream through a conduit (40)/(40a). In such cases, it is particularly preferred that the foldable member (1) is fluid permeable to allow drainage of excess carrier fluid.

The orientation of the placed plant propagules (2) may be defined (i.e. that the plant propagules (2) are placed in a known direction to begin with) or it may be non-defined, whereby it is necessary to perform additional steps to ensure that the plant propagule (2) is in the desired orientation, as discussed below in more detail.

Identifying the Root Forming End (7) and the Shoot Forming End (8) of the Plant Propagule (2) (Step d)

The step (d) of identifying the root forming end (7) and the shoot forming end (8) of the plant propagule (2) may be performed by digital image analysis, as discussed in more detail below in the context of the second aspect of the invention.

In cases where the plant propagule (2) is placed in a known direction in the placement step (c), no further active steps may be necessary and the step can be regarded as optional.

The method may further comprise the additional steps (d') of determining the quality of the propagule (2) by means of by digital image analysis and (d'') of discarding propagules deemed to be of inferior quality, see discussion below in the context of the second aspect of the invention.

Identifying an Imaginary Line (9) Across the Foldable Member (1) Stretching Through the Root Forming End (7) to the Shoot Forming End (8) of the Propagule (Step e)

The step (e) may be performed automatically, based on digital image analysis, as discussed below in the context of the second aspect of the invention.

In cases where the plant propagule (2) is placed in a known direction in the placement step (c), no further active steps may be necessary, as the known direction of the placement in itself may provide sufficient identification of the imaginary line (9), and the step can be regarded as optional.

Folding the Foldable Member (1) (Step f) and Placing the Folded Member into the Hollow Member (3) (Step g)

The foldable member (1) is folded along the imaginary line (9) running through the root-forming end (7) and the shoot-forming end (8) of the propagule, such that the plant propagule (2) becomes wrapped in the folded foldable member (1a).

The folding may be performed using a folding device or arrangement (30,80)/(80,120) as described below in the context of the second aspect of the present invention.

In case the folding is performed using a folding device or arrangement (30,80)/(80,120) having a defined folding axis by which it operates, it may be advantageous or necessary that the step (f) comprises the substeps (f') of rotating the foldable member (1) such that the imaginary line (9) is aligned with a folding axis of a folding device or arrangement (30,80)/(80,120), the substep (f'') of inserting the foldable member (1) into the folding device and the substep (f''') of folding the foldable member (1) by means of the folding device or arrangement.

Alternatively, the steps (f) and (g) may be performed by a folding device or arrangement (80,120) where the foldable member (1) is folded around the propagule (2) by an actuation system, such as sequential gripping folding and sliding actuators (120) described in more detail in the context of the second aspect of the present invention.

The steps (f) and (g) may be performed by a folding device or arrangement where the foldable member (1) is folded around the propagule (2) by holding and sliding the foldable member (1) along a folding platform (30). Such folding device (30, 80) is described in more detail in the context of the second aspect of the present invention.

Once the propagule is placed on the foldable member (1), a folding mechanism be rotated to the desired angle such that the member is folded around the propagule such that the folding axis aligned with the propagule, or in case the angle of the folding mechanism is fixed, the foldable member (1) may be rotated such that the folding is again along the axis of the propagule (2).

Providing a Suitable Growth Medium to Said Plant Propagule (2) (Step h)

After placing the wrapped plant propagule (2) into the hollow member (3), the method comprises the step (h) of providing a suitable growth medium or substrate (170) to said plant propagule (2). The type of growth medium is selected depending on the particular plant propagule (2), and can be any known growth medium known to be suitable for the particular propagule (2). Preferably, the growth medium in step (h) is in liquid form. The type of growth medium will depend on the type of propagule (2), and in general any medium known in the art can be adopted for use with the present invention.

For spruce somatic embryos, the growth medium in step (h) may for example comprise $KNO_3$, $KH_2PO_4$, $NH_4NO_3$, $MgSO_4.7H_2O$, $CaCl_2.2H_2O$, $KI$, $H_3BO_3$, $MnSO_4.H2O$, $NaMoO_4.2H_2O$, $CuSO_4.5H_2O$, $CoCl_2.6H_2O$, $ZnSO_4$, $H_2OFe$, Na-EDTA, Casein hydrolysate, Sucrose, Vitamins comprising Thiamine HCl, and/or Inositol. See for example, von Arnold and Clapham in Methods for Molecular Biology, vol. 427, pages 31-47.

Incubating the Plant Propagule (2) (Step i)

After provision of the growth medium, the method comprises the step (i) of incubating the plant propagule (2) in suitable conditions and for a sufficient time for a root to form, whereby a root (7a) is formed inside said hollow member (3) (step i).

The suitable conditions are selected based on the type of plant propagule (2), and include a suitable temperature and suitable lighting. Suitable conditions are known in the prior art for most types of plant propagules (2). For example, the suitable conditions in step (i) for conifer somatic embryos comprise placing the plant propagule (2) under light at 18-22 degrees Celsius.

As a result, the propagule develops inside the hollow member (3), whereby the root (7a) grows into the hollow member (3) (See FIG. 3B). Therefore, it is achieved that the propagule (2) with the fragile root is located inside the hollow member (3), with no need to manipulate the fragile root to accomplish the placement. Thus, the plant propagule (2) thus placed is subjected to less stress from handling and is how higher quality and higher viability.

An advantage of this method is that the hollow member (3) with the root inside can be coupled to a planting system. This coupling allows planting the plant propagule (2) inside a solid substrate, such as peat moss, as described in the planting methodology (see PCT/IB2014/067084). With the described germination platform, there is no need for a mechanism to place the roots inside the hollow member (3) since the root is already inside a member.

The plant propagules (2) placed within the hollow members (3) may then advantageously planted by way of automated means in a solid growth substrate, as disclosed in PCT/IB2014/067084. The end result is high-throughput automated planting with higher quality of plants and/or higher viability of the propagules.

Further Optional Features of the Method

The method may further comprise the step (j) of planting the plant propagule (2), after the root (7a) has formed in step (i), in a growth substrate, manually or by means of an automated planting system, such as by the method and/or the device disclosed in PCT/IB2014/067084.

Preferably, at least one of the steps is performed by means of a device according to the second aspect of the present invention disclosed below.

A Device for Directionally Placing a Plant Propagule (2) Inside a Hollow Member (3)

In a second aspect, the present invention relates to a device for directionally placing a plant propagule (2) inside a hollow member (3), as exemplarily illustrated in FIGS. 4-7, comprising:
- a) a platform element (20) arranged such that a foldable member (1) can be placed thereon;
- b) an actuating dispensing arrangement (90a, 90b, 100) for placing a foldable member (1) on the platform element (20);
- c) an arrangement (40, 50, 57) or alternatively (40a) for placing a plant propagule (2) on a foldable member (1) placed on the platform element (20);
- d) optionally, means (150) for identifying an imaginary line (9) on the foldable member (1) stretching through the root forming end (7) to the shoot forming end (8) of the propagule (2) being directionally placed during operation;
- e) an actuating folding arrangement (30, 80) or alternatively (120/80) for folding the foldable member (1) along said imaginary line (9) to form a folded foldable member (1a);
- f) an actuating dispensing arrangement (180) for providing a hollow member (3) having a first open end (4);
- g) an actuating placing arrangement (30, 80) or (120/80) for placing said folded foldable member (1a) into the hollow member (3) through the first open end (4).

The device of the second aspect is arranged for performing key steps of the method of the first aspect. Thus, the device is configured such that during operation, the device performs the following functions:
- I. providing a hollow member (3) having a first open end (4) (by actuating dispensing arrangement feature (f));
- II. providing a foldable member (1) (by actuating dispensing arrangement feature (b));
- III. placing a plant propagule (2) on said foldable member (1) (by arrangement for placing a plant propagule (2) feature (c));
- IV. if necessary, identifying the root forming end (7) and the shoot forming end (8) of the plant propagule (2) (by means feature (d));
- V. if necessary, identifying an imaginary line (9) across the foldable member (1) stretching through the root forming end (7) to the shoot forming end (8) of the propagule (by means feature (d));
- VI. folding the foldable member (1) along said imaginary line (9) such that the plant propagule (2) becomes wrapped in the folded foldable member (1a) (by actuating folding arrangement feature (e));
- VII. placing said folded foldable member (1a) with the wrapped plant propagule (2) into the hollow member (3) through the first open end (4) (by actuating placing arrangement feature (g)).

The functions above may, but need not, be performed in the indicated order. Some of the functions may be performed concurrently, e.g. provision functions I and II. In certain embodiments, the process of directional placing of propagules (2) is ongoing and several or all of the functions are being performed concurrently at different locations of the device.

Platform Element (20) (Feature (a))

The device comprises a platform element (20) arranged such that a foldable member (1) can be placed thereon. The device may comprise multiple platform elements (20) arranged on a support element (10), which may be rotatable along an axis (12), allowing the platform elements (20) to be conveniently relocated to and from different positions adapted to perform different stages of the operation. The support element (10) may be configured to support four platform elements (20) to provide for four distinct positions P1-P4 (see FIG. 4C, 6A, 6B).

The four positions P1-P4 illustrated in FIGS. 4C, 6A and 6B are shown implemented on a rotating support element (10). In operation of such embodiments, the foldable member (1) is loaded in position P4, the platform element is rotated by 90 degrees, a plant propagule (2) is deposited in position P1 on the foldable member (1), the platform element is rotated again by 90 degrees. The plant propagule (2) may be imaged in position P2 and the foldable member (1) may be rotated by rotating the platform element at P2 on which the foldable member lies, so that in position P3, which is reached after another 90 degrees' rotation, the plant propagule (2) will be correctly wrapped oriented with the root first going into the hollow member (3). This process can then be repeated with the next plant propagule (2).

Preferably, the platform element (20) is rotatable along an axis (22), allowing alignment of a plant propagule (2) placed on the foldable member (1) with the folding arrangement (30,80) or (80,120) based on input from the means (150). The foldable member (1) may have the features as discussed in the context of the first aspect.

A platform element (20) can be a perforated metallic or plastic screen where the foldable member (1) may reside on top of this perforated platform (see FIG. 4C). The platform element may also comprise other types of support for the foldable member (1) such as a configuration of block support (110) and a tubular member for providing low pressure (115), see FIGS. 6A and 6B.

There can be some vacuum being generated inside of the platform element (20) such that any foldable member (1) placed on the platform element (20) is kept firmly in place.

The platform element (20) may be placed on a shaft (115) that is free to rotate in either direction around it central longitudinal axis (22).

Dispensing Arrangement (Feature (b))

The device comprises an actuating dispensing arrangement (90a, 90b, 100) configured for placing a foldable member (1) on the platform element (20). The dispensing arrangement may comprise a suction device (105) placed on an actuator (100) where the suction device (105) is configured to pick up the foldable member (1) and to place it on top of the platform element (20).

Arrangement for Placing a Plant Propagule (2) (Feature (c))

The device comprises an arrangement (40, 50, 57) or (40a) configured for placing a plant propagule (2) on a foldable member (1) placed on the platform element (20), in a manner disclosed in the context of the first aspect of the present invention. The plant propagule (2) may be as disclosed in the context of the first aspect.

A preferred arrangement (deposition device) can be as the deposition device disclosed in WO2011/042888.

The arrangement for placing a plant propagule (2) on a foldable member (1) placed on the platform element (20) may comprise:
- a) a delivery conduit (40) capable of delivering a stream of fluid comprising plant propagules (2) suspended in the fluid, wherein the delivery conduit (40)/(40a) is located above the platform element (20);
- b) a collection conduit (50) capable of collecting the stream of fluid;
- c) a detector (140) configured for detecting a plant propagule (2) in the stream of fluid in the delivery conduit;
- d) an actuating means (57) configured for reversibly diverting the collection conduit when a plant propagule (2) is detected, operatively connected to the detector (140) for detecting a plant propagule (2);

wherein in operation, the actuating dispensing arrangement (90a, 90b, 100) for placing a foldable member (1) on the platform element (20) places a foldable member (1) on the platform element (20); and when a plant propagule (2) is detected, the actuating means (57) for diverting the collection conduit is activated by the detector (140) for detecting a plant propagule (2) such that the stream of fluid from the delivery conduit places the plant propagule (2) on the foldable member (1), after which the diversion of the collection conduit (50) is reverted to collect the stream of fluid until the next propagule (2) is delivered. It is practically easier to collect the excess fluid in a collection conduit (50) than to flood the platform element (20).

If FIG. 4D an alternative embodiment is shown. At the conduit (40a), there is during operation provided interruptible suction guiding the liquid flow (52) from the top horizontal tube section into the first outlet (41) (shown as lower horizontal tube at the T junction) and preventing the fluid flow from coming out through the second outlet (42) (shown as vertical downward) of the conduit (40a) unless the detector (140) detects a plant propagule (2), such as a somatic embryo, in the flow of fluid.

When a plant propagule (2) is detected, after a very short time delay, length of which is determined depending on the speed of fluid, the suction is interrupted very briefly allowing the plant propagule (2) to drop on the foldable member (1) on platform (20) through the second outlet (42) of the conduit (40a). As soon as the plant propagule (2) leaves the second outlet (42), the suction is resumed guiding the liquid flow back into the first outlet (41) and preventing liquid to flow through the second outlet (42). This way only when there an incoming plant propagule (2), the liquid will flow with the plant propagule (2) on top of the foldable member (1) on the platform element (10), avoiding excessive flooding of the platform element.

The arrangement depicted in 4C with the collection conduit (50) and the method in 4D serve the exact same purpose of only dropping the plant propagule (2) with small amount of liquid on top of the foldable member (1). An advantage in the arrangement of FIG. 4D is that there are no moving parts. Both embodiments require precise timing but work very well.

Means for Identifying Direction of the Propagule (Feature (d))

The device may optionally comprise means (150) for identifying an imaginary line (9) on the foldable member (1) stretching through the root forming end (7) to the shoot forming end (8) of the propagule (2) being directionally placed during operation. Said means may comprise a digital imaging arrangement (150) configured for identifying the root forming end (7) and the shoot forming end (8) of the plant propagule (2) and for identifying an imaginary line (9) on the foldable member (1) stretching through the root forming end (7) to the shoot forming end (8) of the propagule (2).

The means (150) is optional in the case the arrangement (40)/(40a) configured for placing a plant propagule (2) on a foldable member (1) is configured such that it provides the plant propagule (2) in a known orientation whereby the location of the imaginary line (9) is already known. For example, a device for orienting plant propagules disclosed in PCT/US2009/039982 can be used to provide plant propagules in a known orientation. Consequently, performing the functions dependent on the means are only performed if necessary, i.e. when the information is not otherwise already available.

The digital imaging arrangement (150) for identifying the root forming end (7) and the shoot forming end (8) of the plant propagule (2) may comprise a high speed digital camera and image analysis software and a computer which can use the software to analyze the image. An image analysis software that can use certain criteria for determining the orientation of the propagule can be used.

The digital imaging arrangement for identifying an imaginary line (9) on the foldable member (1) stretching through the root forming end (7) to the shoot forming end (8) of the propagule (2) may comprise an imaging system such as a camera and image analysis software and hardware. The imaging software may analyze the digital form of the image to determine the orientation of the propagule by detecting the edges of the propagule (2) and making note of the longest dimension of the propagule (2) and calculating a line (9) through the center of the image in the parallel to the longest dimension.

A suitable means for identifying direction of the propagule for plant somatic embryos is disclosed in PCT/US2009/039982.

In cases the plant propagule (2) is being placed with an arrangement providing the propagule in a known direction, such arrangement for placing a plant propagule (2) may be regarded as means for identifying direction of the propagule.

Optionally, the device may comprise means (150) for determining the quality of the propagule by means of by digital image analysis and means for discarding propagules deemed to be of inferior quality. The quality could be based on many aspects depending on the physical appearance, size and shape of the propagule. This depends on the type of propagule.

Means for Placing a Folded Foldable Member (1) into a Hollow Member (3) (Feature (g)) and Means for Folding the Foldable Member (1) (Feature (e))

The device comprises an actuating placing arrangement (30, 80)/(120/80) configured for placing said folded foldable member (1) into the hollow member (3) through the first open end (4). The placing arrangement may be arranged to place the foldable member (1) such that the root forming end (7) of the propagule is directed away from the first end of said hollow member (3).

The device comprises an actuating folding arrangement configured for folding the foldable member (1) along said imaginary line (9). The folding arrangement may comprise a sliding actuating placing arrangement (80) and a folding platform (30) for a foldable member (1), as exemplified in FIGS. 4B, 4C and 5.

The functions of the actuating folding arrangement and the actuating placing arrangement are preferably combined into a single arrangement. By longer movement of the actuating placing arrangement (80) the foldable member may not only be folded in a folding platform (30) by also passed further through the folding platform (30) and inserted into a hollow member (3).

FIGS. 7A-E illustrate a combined folding and placing arrangement and operation thereof:

FIG. 7A shows the actuating placing arrangement (80) in an uplifted position while the foldable member is forwarded to position P3. The arrow illustrates subsequent downward movement of the arrangement (80).

FIG. 7B shows the arrangement (80) in a lowered position in contact with the foldable member (1).

FIG. 7C shows a movable gripping and sliding actuation mechanism with two arms (120). The left-right arrow illustrates a first axis of movement during operation, and the upward arrow illustrates movement during the folding operation (result illustrated in FIG. 7D).

FIG. 7D shows the gripping and sliding actuation mechanism (120) in a position folding the foldable member (1).

FIG. 7E shows sequentially (top-down) the operation of the arrangement (80) moving to place the folded foldable member (1a) into the first open end (4) of the tubular hollow member (3), followed by the actuating placing arrangement (80) moving up from the folded foldable member to an uplifted position Means for Providing a Hollow Member (3) (Feature (f))

The device comprises an actuating dispensing arrangement (180) configured for providing a hollow member (3) having a first open end (4). The hollow member (3) may be as disclosed in the context of the first aspect.

The dispensing arrangement (180) may comprise linear actuators with capability to move in different directions. The advantages of having the dispensing arrangement (180) on linear actuators (190) that can move in different directions are several fold. One, the hollow member (3) can be placed in staggered arrangement to maximize the number of hollow members (3) per unit area and move diagonally as well as rectangularly to fill the hollow members with the plant propagules (2) inside the folded foldable members (1a). Second, the ability for actuation in different directions allows fine adjustment of the position of the hollow member (3) relative to the folding and actuating placing mechanism (80,120) as shown in FIG. 7A-E.

Optional Means for Orienting the Hollow Member (3)

The device may further comprise an actuating placing arrangement configured for placing said hollow member (3) with the folded foldable member (1) comprising the plant propagule (2) such that the root forming end (7) is directed in a downward.

General Description

The germination platform (GP) described herein is used for housing a plant propagule such as a somatic plant embryo, seed or other plant propagules from micropropagation (hereinafter referred collectively or individually as "SE") through various needed processes including but not limited to storage, dessication, germination and planting. The invented GP is simple and inexpensive, and therefore, cost-effective for producing large number of better quality plants from SE. It allows easy handling and transportation of the germinated propagule. Furthermore, because of the design, it produces more straight and better quality roots.

The GP comprises a foldable member such as a circular paper disk and a hollow elongated member such as a circular tube. The tube may have a slit at the inlet. The SE may be placed at the center of the paper disk, then the paper disk is folded around the SE such that the SE is oriented longitudinally at the base of the folded paper disk, as shown in FIGS. 1 and 2.

The folded paper disk containing the SE may then be placed inside the tube such that the root-end of the SE is pointing in the axial direction of the tube, as illustrated in FIG. 2. The tube with the folded paper disk and SE may then be placed inside a perforated plate. The perforated plate can hold from a few to few thousand tubes at one time.

The perforated plate with the tubes may then be placed inside a sealed container, such that if necessary the entire assembly of tubes and paper disks can be kept sterile during desiccation, germination, and planting. Upon addition of growth medium to the assembly of tubes, after a period of time the roots will grow inside the tube, as illustrated in FIG. 3.

The references cited herein are incorporated by reference in their entirety. The term "comprising" is to be interpreted as "including, but not being limited to".

The arrangement of the present disclosure into sections with headings and subheadings is merely to improve legibility and is not to be interpreted limiting in any way, in particular, the division does not in any way preclude or limit combining features under different headings and subheadings with each other.

EXAMPLES

Example 1

Circular paper disks with SE inside were placed inside tubes made from stereolithography. The tubes were placed inside a perforated plate inside a sealed container, as described above. Germination medium was added to the container so the paper disk and the embryo were soaked with the liquid germination medium. After two weeks, roots and shoots developed where the roots penetrated inside the tube, similar to the illustration in FIG. 3b.

Example 2

Automated loading of the germination platform from the Embryo Selection and Sorting System The embryos can be placed inside the paper disk, disk folded and placed inside the tube manually. In this section we describe a method for automatic preparation and placement of the folded disk with the embryo in the correct orientation inside the tube. The method and the device are described below.

The method involves placing the SE flat on the middle of the foldable member, in this case circular paper disk was used. This could be done from the embryo sorting and deposition system, as described in Patent application WO2011042888 A2, or any other method of depositing the embryo in the middle of the paper disk. Then the SE on the foldable member is identified to determine the orientation in the plane of the paper disk. Identification of the embryo can be by a number of methods such as imaging, sensors or any other identification method. Once the orientation is determined, then the paper disk is rotated so the embryo orientation is always in a designated direction where the folding takes place. Then as the paper disk is folded, the embryo will have the root-end in a designated direction. Note that the paper disk is circular, and therefore, it can rotate relative to the folding mechanism. So if the folding mechanism has a fixed orientation, the paper disc can be folded along any straight line through the center as long as the paper disk is oriented such that the line is aligned with the folding mechanism. Therefore, if the SE is placed flat at the center of the paper disk, then it can be imaged to capture the SE's orientation. The paper disk can then be rotated such that the SE, similar to the straight line, is oriented in alignment with the folding mechanism. In this way the folding mechanism always folds the paper disk such that the SE is aligned as described above. Any number of mechanisms can be designed to place the folded paper disk with the SE inside the tube.

The advantage of this method is that the root will grow inside the tube and therefore, it will be easy to handle, transport, store and plant.

Example 3

Handling of Somatic Norway Spruce Embryos

In one set of experiments, 25 Norway Spruce embryos were placed in the folded paper disk and inserted inside the tube after standard dessication. After 4 weeks, the shoots lengths from the top of the shoot to the middle of the germinant/brown knot part was measured. The longest shoot was measured to be 35 mm and shortest one 12 mm. The average is 15 mm.

From the total of 25 embryos 25 have germinated with a root. Of these 25 germinants, 16 grew into healthy plants after planting in standard peat moss. The yield in this case from the selected embryos to germination is 100% and from selected embryos to plant development is 64%.

The invention claimed is:

1. A plant propagule placing device for directionally placing a plant propagule inside a tubular hollow member, comprising:
   a. a platform element arranged such that a foldable member can be placed thereon;
   b. an actuating foldable member dispensing arrangement for placing the foldable member on the platform element;
   c. an arrangement for placing the plant propagule on the foldable member placed on the platform element;
   d. a means for identifying an imaginary line on the foldable member stretching through a root forming end to a shoot forming end of the plant propagule being directionally placed during operation or the arrangement is configured for placing a plant propagule on a foldable member such that the foldable member provides the plant propagule in a known orientation thus identifying the location of the imaginary line;
   e. an actuating folding arrangement for folding the foldable member along said imaginary line to form a folded foldable member;
   f. an actuating tubular dispensing arrangement for providing the tubular hollow member having a first open end; and
   g. an actuating placing arrangement for placing said folded foldable member into the tubular hollow member through the first open end;
   wherein the actuating folding arrangement is configured to also function as an actuating placing arrangement;
   wherein the device is configured for performing a method for directionally placing the plant propagule inside the tubular hollow member, such that during operation, the device performs the steps of:
   I. providing the tubular hollow member having a first open end by means of the actuating, hollow-member-dispensing arrangement;
   II. providing the foldable member, and placing the foldable member on the platform element by means of the actuating, foldable-member-dispensing arrangement;
   III. placing a plant propagule on said foldable member placed on the platform element by means of an arrangement;
   IV. identifying the root forming end and the shoot forming end of the plant propagule and identifying the imaginary line across the foldable member stretching through the root forming end to the shoot forming end of the plant propagule, by the means for identifying an imaginary line;
   V folding the foldable member along said line by means of the actuating folding arrangement such that the plant propagule becomes wrapped in the folded foldable member; and
   VI. placing said folded foldable member with the wrapped plant propagule into the tubular hollow member through the first open end by means of the actuating placing arrangement.

2. The device according to claim 1, wherein the platform element is rotatable along an axis.

3. The device according to claim 1, wherein the platform element is arranged on a support element rotatable along an axis.

4. The device according to claim 1, comprising four or more platform elements.

5. The device according to claim 1, wherein the actuating foldable member dispensing arrangement for placing the foldable member on the platform element comprises a suction device placed on an actuator wherein the suction device is configured for picking up the foldable member and placing the foldable member on top of the platform element during operation.

6. The device according to claim 1, wherein the arrangement for placing a plant propagule on the foldable member placed on the platform element comprises:
   a. a delivery conduit capable of delivering a stream of fluid comprising plant propagules suspended in the fluid, wherein the delivery conduit is located above the platform element;
   b. a collection conduit capable of collecting the stream of fluid;
   c. a detector for detecting the plant propagule in the stream of fluid in the delivery conduit;
   d. an actuating means for reversibly diverting the collection conduit when the plant propagule is detected, operatively connected to the detector for detecting the plant propagule;
   wherein the device is configured such that in operation, the actuating foldable member dispensing arrangement for placing the foldable member on the platform element places the foldable member on the platform element; and
   when the plant propagule is detected in the stream of fluid in the delivery conduit, the actuating means for diverting the collection conduit is activated by the detector for detecting the plant propagule such that the stream of fluid from the delivery conduit places the plant propagule on the foldable member, after which the diversion of the collection conduit is reverted by the actuating means in preparation of a second propagule.

7. The device according to claim 1, wherein the arrangement for placing the plant propagule on the foldable member placed on the platform element comprises:

a conduit having a first outlet and a second outlet capable of delivering a stream of fluid comprising plant propagules suspended in the fluid, wherein the second outlet of the conduit is located above the platform element, and wherein the first outlet is arranged such that the first outlet may be provided with interruptible suction during operation; and a detector for detecting the plant propagule in the stream of fluid in the conduit;

wherein the device is configured such that during operation, the actuating foldable member dispensing arrangement for placing the foldable member on the platform element places the foldable member on the platform element;

wherein, in a default state, the first outlet is provided with a suction such that the stream of fluid is prevented from exiting through the second outlet; and wherein when the plant propagule is detected in the stream of fluid in the delivery conduit, the suction through the first outlet is interrupted for a time such that the plant propagule exits through the second outlet with the stream of fluid and becomes placed onto the foldable member, after which the suction through the first outlet is resumed.

8. The device according to claim 1, wherein the actuating folding arrangement for folding the foldable member along said imaginary line comprises a sliding linear actuator and a folding platform for the foldable member.

9. The device according to claim 1, wherein said means for identifying the imaginary line on the foldable member comprises a digital imaging arrangement for identifying the root forming end and the shoot forming end of the plant propagule and for identifying an imaginary line on the foldable member stretching through the root forming end to the shoot forming end of the plant propagule.

10. The device according to claim 1, wherein the actuating tubular hollow member dispensing arrangement for providing the tubular hollow member comprises linear actuators having the capacity of moving in different directions during operation.

11. The device according to claim 1, wherein the actuating placing arrangement for placing said folded foldable member into the tubular hollow member through the first open end such that the root forming end of the plant propagule is directed away from the first end of said tubular hollow member comprises a gripping and sliding actuation mechanism and a sliding linear actuator, wherein the device is configured such that during operation, the following is performed by the device:

a. the actuator is moved to become located on top of the foldable member with a plant propagule;

b. the gripping and sliding actuation mechanism is moved to fold the foldable member along the imaginary line; and c. the folded foldable member is held in place by the sliding linear actuator and the gripping and sliding actuation mechanism which move the folded foldable member into the tubular hollow member, after which the sliding linear actuator is lifted and the gripping and sliding mechanism is disengaged, thereby placing the folded foldable member in the tubular hollow member.

12. The device according to claim 1, wherein the actuating folding arrangement is configured to function as an actuating placing arrangement.

13. The device according to claim 1, comprising a means for identifying an imaginary line on the foldable member stretching through the root forming end to the shoot forming end of the plant propagule, wherein the plant propagule is directionally placed during operation, and wherein the means is configured such that during operation the means identifies the root forming end and the shoot forming end of the plant propagule and identifies the imaginary line across the foldable member stretching through the root forming end to the shoot forming end of the plant propagule.

14. A method for growing a root from a plant propagule inside a tubular hollow member comprising:

a. providing the tubular hollow member having a first open end;

b. providing a foldable member;

c. placing a plant propagule on said foldable member;

d. identifying a root forming end and a shoot forming end of the plant propagule;

e. identifying an imaginary line across the foldable member stretching through the root forming end to the shoot forming end of the plant propagule by means of a device according to claim 1;

f. folding the foldable member along said line such that the plant propagule is wrapped in the folded foldable member;

g. placing said folded foldable member with the wrapped plant propagule into the tubular hollow member through the first open end;

h. providing a plant growth medium to the wrapped plant propagule;

i. incubating the wrapped plant propagule in conditions supporting root formation until a root forms, whereby the root is formed inside said tubular hollow member;

wherein the method is carried out with a device for directionally placing the plant propagule inside the tubular hollow member, comprising:

a platform element arranged such that the foldable member can be placed thereon;

a actuating foldable member dispensing arrangement for placing the foldable member on the platform element;

an arrangement for placing the plant propagule on the foldable member placed on the platform element;

a means for identifying an imaginary line on the foldable member stretching through the root forming end to the shoot forming end of the plant propagule, wherein the plant propagule is directionally placed during operation;

an actuating folding arrangement for folding the foldable member along said imaginary line to form a folded foldable member;

a actuating hollow tubular member dispensing arrangement for providing the tubular hollow member having the first open end; and an actuating placing arrangement for placing said folded foldable member into the tubular hollow member through the first open end.

15. The method according to claim 14, wherein placing said folded foldable member with the wrapped plant propagule into the tubular hollow member through the first open end further comprises placing the folded foldable member such that the root forming end of the propagule is directed away from the first end of said tubular hollow member.

16. The method according to claim 14, wherein the tubular hollow member is elongated and has a second end and, and wherein the tubular hollow member is tapered such that the tubular hollow member has a smaller cross-sectional area at the second end compared to the first end.

17. The method according to claim 14, wherein the tubular hollow member is open at the second end.

18. The method according to claim 14, wherein the tubular hollow member comprises a notch or a slot at the first end.

19. The method according to claim 14, wherein the tubular hollow member is formed by wrapping a sheet.

20. The method according to claim 14, wherein the foldable member comprises paper, a flexible plastic material, or both paper and the flexible plastic material.

21. The method according to claim 14, wherein the plant propagule is placed at the center region of the foldable member.

22. The method according to claim 14, wherein the plant propagule is placed on the foldable member by means of a fluid stream.

23. The method according to claim 14, wherein the growth medium is in liquid form.

24. The method according to claim 14, wherein the plant propagule is a plant tissue fragment, a plant callus fragment, or a plant somatic embryo.

25. The method according to claim 24, wherein the plant propagule is a somatic embryo.

26. The method according to claim 25, wherein the plant propagule is a conifer somatic embryo.

27. The method according to claim 26, wherein the plant propagule is a spruce somatic embryo.

28. The method according to claim 27, wherein the plant propagule is a Norway spruce somatic embryo.

29. The method according to claim 27, wherein the plant growth conditions comprise placing the plant propagule under light at 18-22 degrees Celsius.

30. The method according to claim 14, further comprising planting the plant propagule in a plant growth substrate, manually or by means of an automated planting system.

* * * * *